(12) United States Patent
Levitzki et al.

(10) Patent No.: US 8,759,363 B2
(45) Date of Patent: Jun. 24, 2014

(54) QUINAZOLINE-BASED T CELL PROLIFERATION INHIBITORS

(75) Inventors: Alexander Levitzki, Jerusalem (IL); Idit Sagiv, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 13/575,573

(22) PCT Filed: Jan. 27, 2011

(86) PCT No.: PCT/IL2011/000093
§ 371 (c)(1),
(2), (4) Date: Jan. 14, 2013

(87) PCT Pub. No.: WO2011/092695
PCT Pub. Date: Aug. 4, 2011

(65) Prior Publication Data
US 2013/0109706 A1 May 2, 2013

Related U.S. Application Data

(60) Provisional application No. 61/299,071, filed on Jan. 28, 2010.

(51) Int. Cl.
*A01N 43/90* (2006.01)
*A61K 31/522* (2006.01)

(52) U.S. Cl.
USPC ............ 514/266.23; 514/266.22; 514/266.24; 514/266.4; 544/284; 544/293

(58) Field of Classification Search
USPC ................. 514/266.2, 266.23, 266.24, 266.4; 544/284, 293
See application file for complete search history.

(56) References Cited

U.S. PATENT DOCUMENTS 6,476,031 B1 11/2002 Chakravarty et al.

FOREIGN PATENT DOCUMENTS

| EP | 1277738 A1 | 1/2003 |
|---|---|---|
| WO | 02/076976 A2 | 10/2002 |
| WO | 2008157500 A1 | 12/2002 |
| WO | 03/049739 A1 | 6/2003 |
| WO | 03/059913 A1 | 7/2003 |
| WO | 03/097615 A1 | 11/2003 |
| WO | 03/104230 A1 | 12/2003 |
| WO | 2008054599 A2 | 5/2008 |
| WO | WO 2008054599 A2 * | 5/2008 |
| WO | WO 2008157500 A1 * | 12/2008 |

OTHER PUBLICATIONS

Sagiv-Barfi et al.: "Design, synthesis, and evaluation of quinazoline T cell proliferation inhibitors", Bioorganic & Medicinal Chemistry, vol. 18, No. 17, pp. 6404-6413 (2010).
Levitzki et al.: "Tyrphostins and other tyrosine kinase inhibitors." Annu Rev Biochem, 75, pp. 93-109 (2006).
Brasca et al.: "Identification of N,1,4,4-tetramethyl-8-{[4-(4-methylpiperazin-1-yl)phenyl]amino}-4,5-dihydr 0-1H-pyrazolo[4,3-h]quinazoline-3-carboxamide (PHA-848125), a potent, orally available cyclin dependent kinase inhibitor." Journal of Medicinal Chemistry, 52(16), pp. 5152-5163 (2009).
Aherne et al.: "Comparison of plasma and tissue levels of ZD1694 (Tomudex), a highly polyglutamatable quinazoline thymidylate synthase inhibitor, in preclinical models.", British Journal of Cancer 77(2), pp. 221-226 (1998).
Jones et al.: "A potent antitumour quinazoline inhibitor of thymidylate synthetase: synthesis, biological properties and therapeutic results in mice", European Journal of Cancer 17(1), pp. 11-29 (1981).
Skelton et al.: "Cell cycle effects of CB30865, a lipophilic quinazoline-based analogue of the antifolate thymidylate synthase inhibitor ICI 198583 with an undefined mechanism of action", Cytometry, 33, pp. 56-66 (1998).
Theti et al.: "Selective delivery of CB300638, a cyclopenta[g]quinazoline-based thymidylate synthase inhibitor into human tumor cell lines overexpressing the alpha-isoform of the folate receptor", Cancer Research, 63, pp. 3612-3618 (2003).

* cited by examiner

*Primary Examiner* — Wu-Cheng Winston Shen
*Assistant Examiner* — Jean Cornet
(74) *Attorney, Agent, or Firm* — Browdy and Neimark PLLC

(57) ABSTRACT

Quinazoline derivatives are provided that specifically inhibit proliferation of T cells without affecting the level of IL-2 secreted from said T cells. These compounds as well as pharmaceutical composition comprising them are useful for the treatment of indications mediated by T cell proliferation.

19 Claims, 20 Drawing Sheets

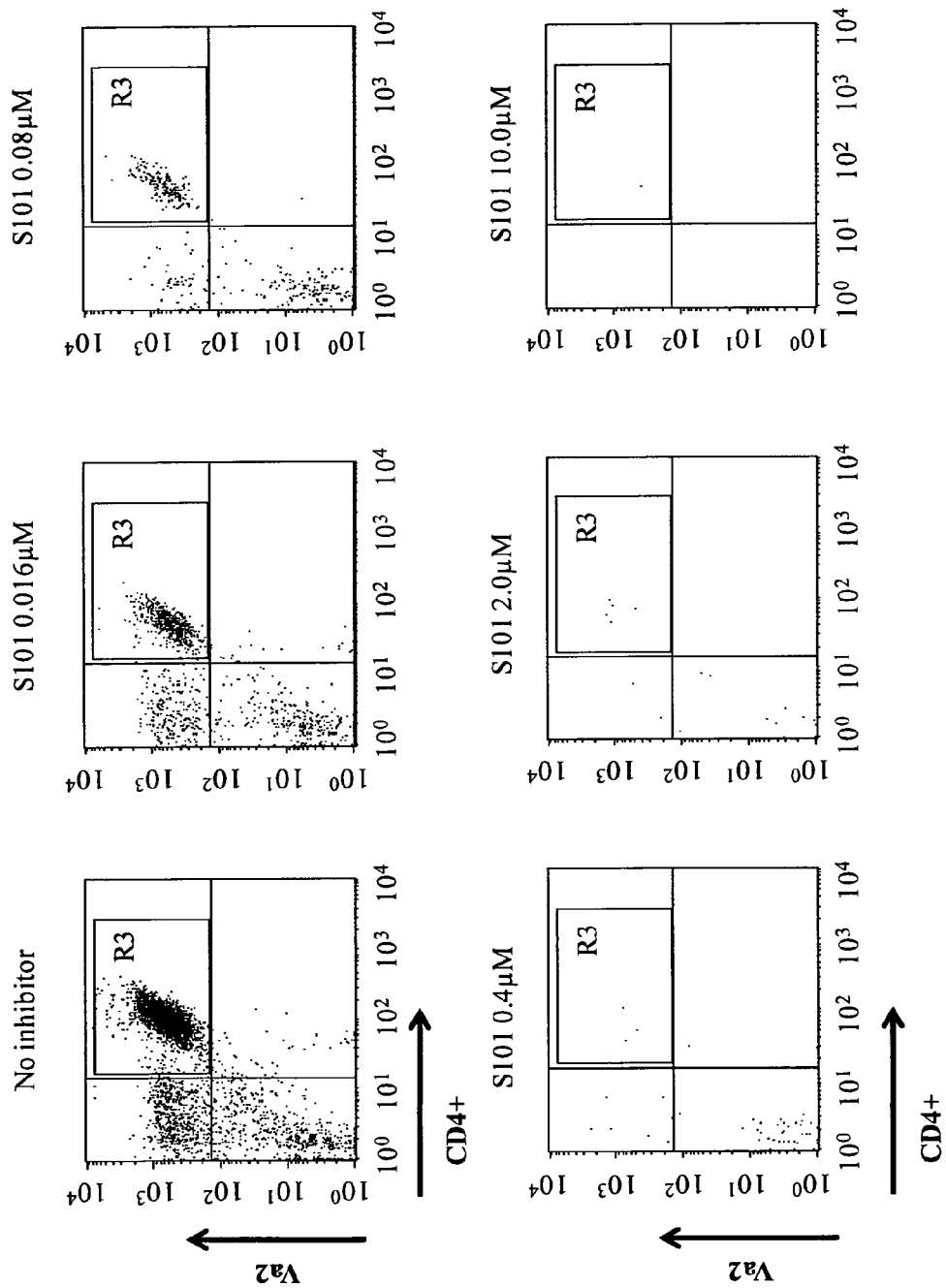

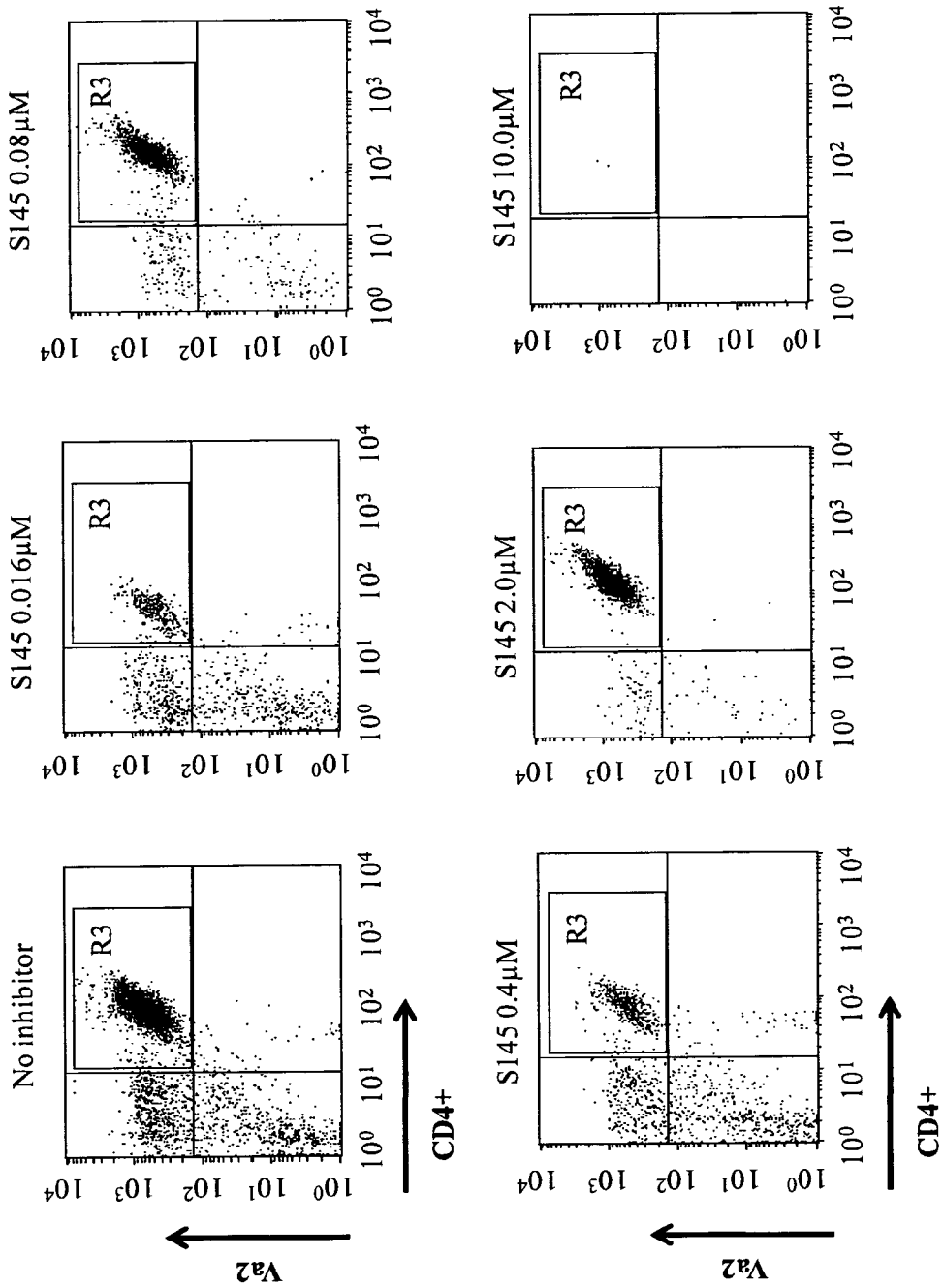

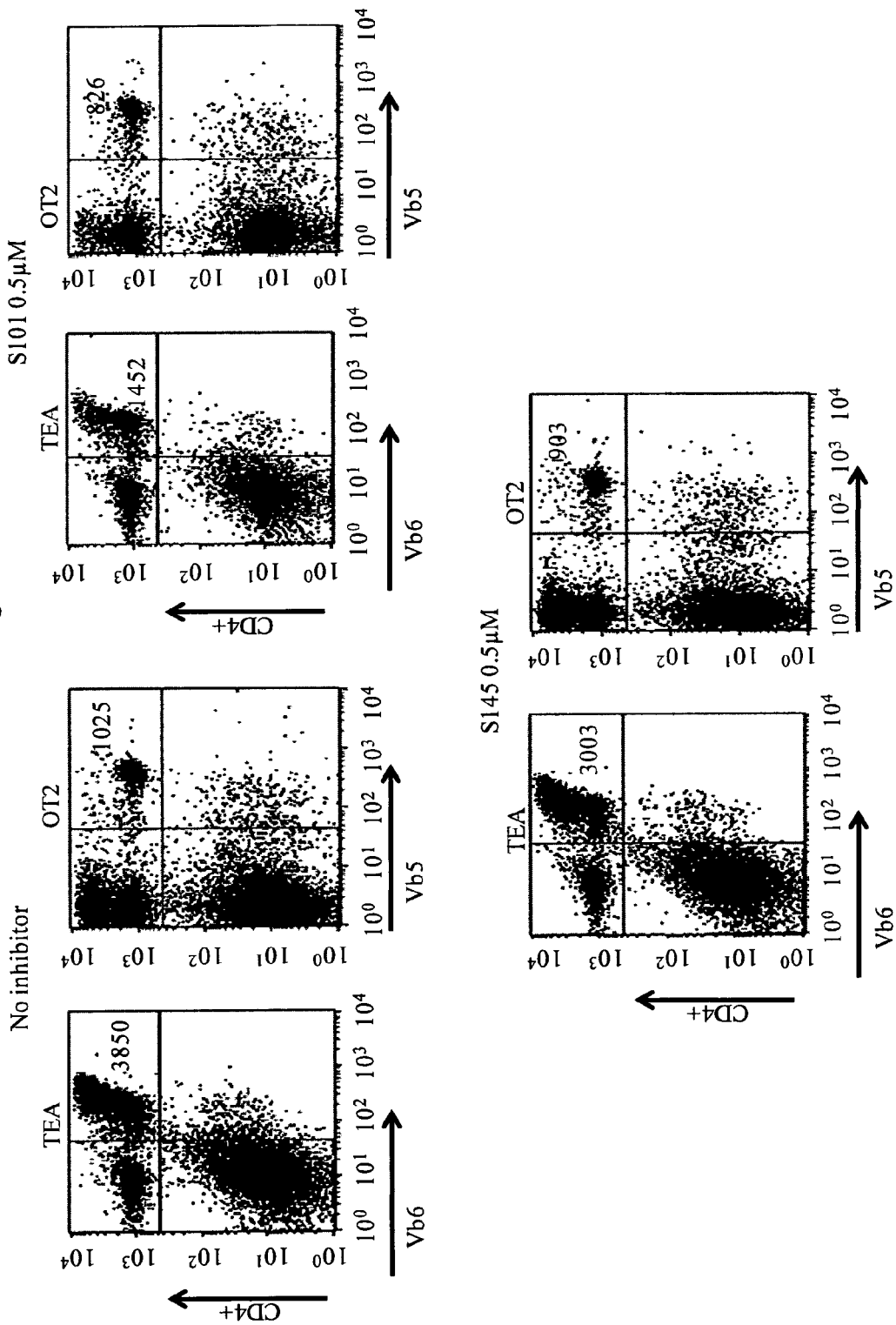

QUINAZOLINE-BASED T CELL PROLIFERATION INHIBITORS

TECHNICAL FIELD

The present invention relates to quinazoline derivatives and their use for treatment of an indication mediated by T cell proliferation.

BACKGROUND

Organ transplantation elicits a complex series of immunologic processes that are generally categorized as inflammation, immunity, tissue repair and structural reinforcement of damaged tissues. Macrophages and T cells mediate inflammation by the secretion of proinflammatory cytokines, e.g., interleukin-2 (IL-2), and by the activation of biochemical cascades such as the classic complement cascade. The medical community is in need of novel immunosuppressive agents [Chiu et al., 2004]. Immunosuppressive drugs fall into five groups: (i) regulators of gene expression; (ii) alkylating agents; (iii) inhibitors of de novo purine synthesis; (iv) inhibitors of de novo pyrimidine synthesis; and (v) inhibitors of kinases and phosphatases [Allison, 2000]. Glucocorticoids exert immunosuppressive and anti-inflammatory activity mainly by inhibiting the expression of the genes for IL-2 and other mediators [Ong et al., 2007]. Cyclophosphamide suppresses immune responses mediated by B-lymphocytes [Turk, 1964; Rollinghoff et al., 1977]. Methotrexate and its polyglutamate derivatives suppress inflammatory responses through release of adenosine [Turk, 1964]. Mycophenolic acid and mizoribine inhibit inosine monophosphate dehydrogenase [Allison et al., 1991; Itoh, 1993]. Mycophenolic acid induces apoptosis of activated T-lymphocytes [Dayton et al., 1992; Cohn et al., 1999]. A leflunomide metabolite and brequinar inhibit dihydroorotate dehydrogenase [Waer, 1996; Herrmann et al., 2000]. Cyclosporine and FK-506/Tacrolimus inhibit the phosphatase activity of calcineurin [Curtis, 1986; Kino et al., 1987; Liu et al., 1991; Herman, 1999; Hojo et al., 1999]. Rapamycin inhibits signal transduction from the IL-2, epidermal growth factor and other cytokine receptors [Gonzalez et al., 2001]. Immunosuppressive and anti-inflammatory compounds in development include inhibitors of p38 kinase and of the type IV isoform of cyclic AMP phosphodiesterase, which is expressed in lymphocytes and monocytes [Thomson, 1994; Abraham et al., 1996; Dodge, 1999].

Immunosuppressive medications are associated with toxicity due to their non-specific immunosuppressive effects. Reducing immunosuppression can prevent side effects related to over-immunosuppression. However, since the intrinsic immunosuppressive requirements for each donor recipient pair are unknown, immunosuppressive minimization carries a potential risk of under-immunosuppression and consequent acute rejection, premature graft loss and death. A promising future application of immunosuppressive drugs is their use in regimens designed to induce tolerance to allografts. The first step in finding such drugs is a search for agents that inhibit T cell proliferation by novel mechanisms, as the currently used agents, which all possess non-specific broad immunosuppressive effects. In our search for compounds that inhibit T cell proliferation we chose a known chemical scaffold, the quinazoline moiety, which has been utilized to develop tyrosine phosphorylation inhibitors. Quinazolines serve as the backbone for a range of inhibitors. Quinazoline-based tyrosine kinase inhibitors include: the reversible EGFR inhibitors, Gefitinib/Iressa/ZD1839 and Erlotinib/Tarceva; the dual EGFR-HER2 inhibitor, Lapatinib/Tykerb/GW572016; and the irreversible EGFR inhibitor, CI-1033 (reviewed in [Levitzki et al., 2006]). Quinazolines also form the basis for inhibitors of serine/threonine kinases, such as CDK [Brasca et al., 2009] and for a thymidylate synthase inhibitor [Jones et al., 1981; Aherne et al., 1998; Skelton et al., 1998; Theti et al., 2003].

EP 1277738A1 discloses fused heteroaryl derivatives, which are useful as medicaments, more particularly as phosphatidylinositol 3-kinase (PI3K) inhibitors and carcinostatic agents.

WO 02/076976 and WO 03/059913 teach quinazoline based compounds, their syntheses and use as Rho-kinase inhibitors. These compounds are said to be useful for inhibiting tumor growth, treating erectile dysfunction, and treating other indications mediated by Rho-kinase, e.g., coronary heart disease.

WO 03/049739 discloses pyrimidine-based compounds useful as gsk-3 inhibitors and their use in the treatment of various protein kinase mediated disorders, such as diabetes, cancer, stroke and Alzheimer's disease.

WO 03/104230 discloses bicyclic pyrimidine derivatives, said to have anti-inflammatory effect and an effect of controlling the function(s) of the Th2 cell chemoattractants TARC and/or MDC.

WO 03/097615 and U.S. Pat. No. 6,476,031B1 are directed to quinazoline derivatives and their use for inhibiting TGF-β and/or p38-α kinase.

SUMMARY OF INVENTION

It has been found, in accordance with the present invention, that certain quinazoline-based compounds, more particularly 2-(3,4,5-trimethoxyphenyl)quinazolin-4-amine and 5-(4-aminoquinazolin-2-yl)benzene-1,2,3-triol derivatives, are capable of inhibiting T cell proliferation. As particularly found, these compounds inhibit the proliferation of T cells from human peripheral blood mononuclear cells (PBMC) and Jurkat cells, with $IC_{50}$ values in the sub-micromolar range. The inhibitors induce G2 cell cycle arrest but, surprisingly, do not inhibit IL-2 secretion. The inhibitors restrain proliferation of lymphocytes with much higher potency than non-hematopoietic cells including several types of cancer cells. The apparent selective effect of these compounds on T cells and its lower activity against other cell types indicate that they are useful in treating indications mediated by T cell proliferation, such as psoriasis and graft rejection diseases.

In one aspect, the present invention thus relates to a method for treatment of indications mediated by T cell proliferation in an individual in need thereof, comprising administering to said individual a therapeutically effective amount of a compound of the general formula I:

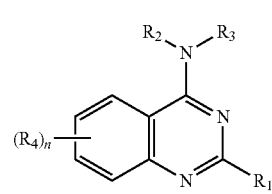

or a pharmaceutically acceptable salt or solvate thereof, wherein $R_1$ is $(C_6$-$C_{10})$aryl substituted by 1 to 5, preferably 3 or 4, —$OR_3$ groups;

R$_2$ is —(CH$_2$)$_n$-heteroaryl, or —(CH$_2$)$_n$—(C$_6$-C$_{10}$)aryl substituted by one or more groups each independently selected from Hal, (C$_1$-C$_8$)alkyl, (C$_1$-C$_8$)alkylene-OH, —NHR$_3$, —OR$_3$, or —O—(CH$_2$)$_n$—C(Hal)$_3$, wherein two —OR$_3$ groups linked to two adjacent carbon atoms of said aryl, together with the carbon atoms to which they are attached, form 1,3-dioxolane ring or 1,4-dioxane ring;

R$_3$ each independently is H or (C$_1$-C$_8$)alkyl;

R$_4$ is absent or 1 to 4 substituents each independently selected from (C$_1$-C$_8$)alkyl, (C$_2$-C$_8$)alkenyl, (C$_2$-C$_8$)alkynyl, (C$_3$-C$_8$)cycloalkyl, (C$_6$-C$_{10}$)aryl, heteroaryl, Hal, —NO$_2$, —CN, —OR$_5$, —SR$_5$, —SOR$_5$, —SO$_2$R$_5$, —COR$_5$, —CO$_2$R$_5$, —CONR$_3$R$_5$, —SO$_2$NR$_3$R$_5$, —NR$_3$R$_5$, —OCONR$_3$R$_5$, —NR$_3$—COR$_5$, NR$_3$—CO$_2$R$_5$, or —NR$_3$SO$_2$R$_5$;

R$_5$ is H, (C$_1$-C$_8$)alkyl, (C$_3$-C$_8$)cycloalkyl, (C$_6$-C$_{14}$)aryl, or heteroaryl;

m is an integer of 0-5; and n is an integer of 1-4, wherein each one of said (C$_1$-C$_8$)alkyl, (C$_2$-C$_8$)alkenyl, or (C$_2$-C$_8$)alkynyl is optionally substituted by one or more groups each independently selected from Hal, —NO$_2$, —CN, —OR$_5$, —SO$_2$R$_3$, —NR$_3$R$_5$, (C$_6$-C$_{10}$)aryl, or heteroaryl; and each one of said (C$_6$-C$_{10}$)aryl, or heteroaryl is optionally substituted by one or more groups each independently selected from (C$_1$-C$_8$)alkyl, (C$_2$-C$_8$)alkenyl, (C$_2$-C$_8$)alkynyl, Hal, —OR$_5$, —SO$_2$R$_3$, —NO$_2$, —NR$_3$R$_5$, —CN, or —C(Hal)$_3$.

In another aspect, the present invention provides a topical composition comprising a compound of the general formula I as defined above, or a pharmaceutically acceptable salt or solvate thereof, and a pharmaceutically acceptable carrier. The topical composition of the invention is preferably useful for treatment of psoriasis.

In still another aspect, the present invention provides a compound of the general formula I as defined above, or a pharmaceutically acceptable salt or solvate thereof, for use in the treatment of indications mediated by T cell proliferation.

In yet another aspect, the present invention relates to use of a compound of the general formula I as defined above, or a pharmaceutically acceptable salt or solvate thereof, for the preparation of a pharmaceutical composition for the treatment of indications mediated by T cell proliferation.

In a further aspect, the present invention provides a compound of the general formula II:

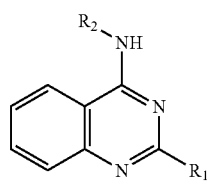

II or a pharmaceutically acceptable salt or solvate thereof, wherein

R$_1$ is trimethoxyphenyl or trihydroxyphenyl; and

R$_2$ is phenyl, 4-methylphenyl, 2,4-dimethylphenyl, 4-hydroxyphenyl, 4-methoxyphenyl, 4-octyloxyphenyl, 4-trifluoromethoxyphenyl, 4-chlorophenyl, benzyl, 4-aminobenzyl, 3,4-difluorobenzyl, 3,4-dichlorobenzyl, 4-methoxybenzyl, or 2-hydroxymethylphenyl.

In still a further aspect, the present invention provides a pharmaceutical composition, such as a topical composition, comprising a compound of the general formula II as defined above, or a pharmaceutically acceptable salt or solvate thereof, and a pharmaceutically acceptable carrier. The pharmaceutical compositions of the invention are useful for treatment of various diseases, disorders and conditions associated with T cell proliferation.

BRIEF DESCRIPTION OF DRAWINGS

FIGS. 7A-F show that compound 2 (S101) has the ability to inhibit CD4+ and CD8+ populations. 2C and TEA responder splenocytes were incubated with irradiated BALB/c or CB6/F1 respectively for 72 h in the presence or absence of the inhibitor. The numbers of double-positive CD8+1B2+/CD4+/Va2 cells were counted during one minute and the proliferation percentage was calculated. FACS analysis of CD8+ (A and B) or CD4+ (C and D) cells treated with S101 (A, C) or S145 (B, D). E. Percentage of cells treated with S101 or S145 that were positively stained with Annexin V. Black bars, CD8+; White bars, CD4+. F. Cell proliferation of cells treated with S101 or S145. Black bars, CD8+; White bars, CD4+.

FIGS. 9A-D show the effect of compound 2 (S101) on proliferating and non-proliferating and CD4+ T cells. OT2 were incubated in the CD4+ (TEA cells) MLR cultures with or without IL-7 in the presence or absence of the inhibitor. A. FACS dot plot comparison of cell numbers after 72 h MLR. B. FACS histogram plot of the Anexin V positive cells. C and D. Cells numbers and Annexin V positive cells, respectively.

DETAILED DESCRIPTION OF THE INVENTION

Figure 1A:
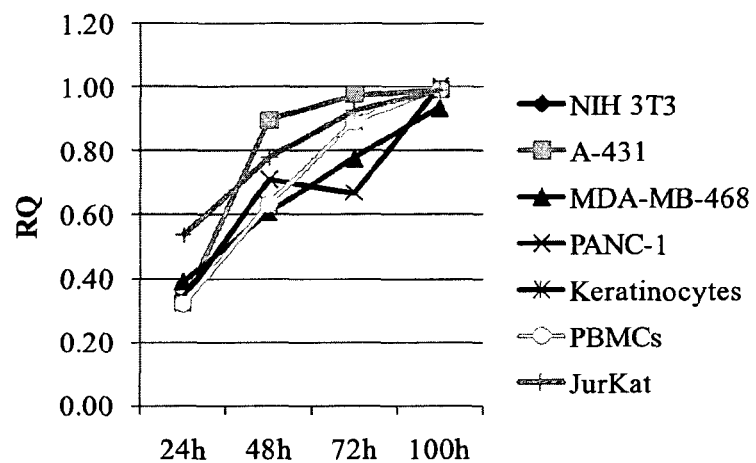
FIGS. 1A-B depict the effect of compound 2 (S101) on the growth of various cell lines. A. BrdU uptake of the cells without stimulation B. BrdU uptake of the stimulated cells: ConA (10 µg/ml) activated PBMC, serum activated HEK293 and A375 and Keratinocytes, PDGF (30 ng/ml) activated NIH 3T3, EGF (30 ng/ml) activated MDA-MB-231 were treated with increasing inhibitor concentrations. Relevant quantification (RQ) to growth without inhibitor's treatment.

In one aspect, the present invention provides a method for treatment of an indication mediated by T cell proliferation by administration of a compound of the general formula I as defined above, or a pharmaceutically acceptable salt or solvate thereof.

The term "Hal" as used herein refers to a halogen and includes fluoro, chloro, bromo, and iodo, and it is preferably fluoro or chloro.

The term "alkyl" as used herein typically means a straight or branched saturated hydrocarbon radical having 1-8 carbon atoms and includes, e.g., methyl, ethyl, n-propyl, isopropyl, n-butyl, sec-butyl, isobutyl, tert-butyl, n-pentyl, 2,2-dimethylpropyl, n-hexyl, n-heptyl, n-octyl, and the like. Preferred are ($C_1$-$C_6$)alkyl groups, more preferably ($C_1$-$C_4$)alkyl groups, most preferably methyl and ethyl. The terms "alkenyl" and "alkynyl" typically mean straight and branched hydrocarbon radicals having 2-8 carbon atoms and 1 double or triple bond, respectively, and include ethenyl, propenyl, 3-buten-1-yl, 2-ethenylbutyl, 3-octen-1-yl, 3-nonenyl, 3-decenyl, and the like, and propynyl, 2-butyn-1-yl, 3-pentyn-1-yl, 3-hexynyl, 3-octynyl, and the like. $C_2$-$C_6$ alkenyl and alkynyl radicals are preferred, more preferably $C_2$-$C_4$ alkenyl and alkynyl.

The term "alkylene" typically means a divalent straight or branched hydrocarbon radical having 1-8 carbon atoms and includes, e.g., methylene, ethylene, propylene, butylene, 2-methylpropylene, pentylene, 2-methylbutylene, hexylene, 2-methylpentylene, 3-methylpentylene, 2,3-dimethylbutylene, heptylene, octylene, and the like. Preferred are ($C_1$-$C_4$) alkylene, most preferably ($C_1$-$C_2$)alkylene.

The term "cycloalkyl" as used herein means a cyclic or bicyclic hydrocarbyl group having 3-8 carbon atoms such as cyclopropyl, cyclobutyl, cyclopentyl, cyclohexyl, cycloheptyl, cyclooctyl, bicyclo[3.2.1]octyl, bicyclo[2.2.1]heptyl, and the like. Preferred are ($C_5$-$C_8$)cycloalkyls, more preferably ($C_5$-$C_6$)cycloalkyls.

The term "aryl" denotes an aromatic carbocyclic group having 6-10 carbon atoms consisting of a single ring or multiple rings either condensed or linked by a covalent bond such as, but not limited to, phenyl, and naphthyl.

The term "heteroaryl" refers to a 6- to 10-membered radical derived from a mono- or poly-cyclic heteroaromatic ring containing one to three, preferably 1-2, heteroatoms selected from the group consisting of N, O and S. When the heteroaryl is a monocyclic ring, it is preferably a radical of a 5-6-membered ring such as, but not limited to, pyrrolyl, furyl, thienyl, thiazinyl, pyrazolyl, pyrazinyl, imidazolyl, oxazolyl, isoxazolyl, thiazolyl, isothiazolyl, pyridyl, pyrimidinyl, 1,2,3-triazinyl, 1,3,4-triazinyl, and 1,3,5-triazinyl. Polycyclic heteroaryl radicals are preferably composed of two rings such as, but not limited to, benzofuryl, isobenzofuryl, benzothienyl, indolyl, quinolinyl, isoquinolinyl, imidazo[1,2-a]pyridyl, benzimidazolyl, benzthiazolyl, benzoxazolyl, pyrido[1,2-a]pyrimidinyl and 1,3-benzodioxinyl. The heteroaryl may be substituted. It is to be understood that when a polycyclic heteroaryl is substituted, the substitution may be in any of the carbocyclic and/or heterocyclic rings.

The chemical synthesis of the compounds used in the present invention is described in the Examples hereinafter. In certain embodiments, the compound used according to the method of the present invention is a compound of the general formula I, wherein $R_1$ is phenyl substituted by 1 to 5, preferably 3 or 4, more preferably 3, —$OR_3$ groups; and $R_3$ each is H or ($C_1$-$C_4$)alkyl, preferably methyl or ethyl. In particular embodiments, the compound used is a compound of the general formula I, wherein $R_1$ is phenyl substituted at each one of positions 3, 4 and 5 by —$OR_3$ group wherein $R_3$ is H or methyl.

In certain embodiments, the compound used according to the method of the present invention is a compound of the general formula I, wherein $R_2$ is —$(CH_2)_n$-heteroaryl, or —$(CH_2)_n$-phenyl substituted by one or more groups each independently selected from F, Cl, ($C_1$-$C_4$)alkyl, preferably methyl or ethyl, ($C_1$-$C_4$)alkylene-OH, preferably ($C_1$-$C_2$) alkylene-OH, —$NH_2$, —O—$(CH_2)_m$—C(Hal)$_3$, or —$OR_3$, wherein $R_3$ is H, methyl or ethyl, or two —$OR_3$ groups linked to two adjacent carbon atoms of said aryl, together with the carbon atoms to which they are attached, form 1,3-dioxolane ring or 1,4-dioxane ring. In particular embodiments, the compound used is a compound of the general formula I, wherein $R_2$ is phenyl, 4-methyl phenyl, 2,4-dimethyl phenyl, 4-hydroxy phenyl, 4-methoxy phenyl, 4-octyloxy phenyl, 4-trifluoromethoxy phenyl, 4-chloro phenyl, 2-hydroxymethylphenyl, benzyl, 4-aminobenzyl, 3,4-difluoro benzyl, 3,4-dichloro benzyl, 4-methoxy benzyl, 1H-indazol-6-yl, 1H-indazol-5-yl, 2-(1H-indol-3-yl)-ethyl, benzo[1,3]dioxol-5-yl, or 3H-benzoimidazol-5-yl.

In certain embodiments, the compound used according to the method of the present invention is a compound of the general formula I, wherein $R_3$ is H or $(C_1-C_4)$alkyl, preferably methyl or ethyl. In particular embodiments, the compound used is a compound of the general formula I, wherein $R_3$ is H.

In certain embodiments, the compound used according to the method of the present invention is a compound of the general formula I, wherein $R_4$ is absent or 1 to 2 substituents each independently selected from $(C_1-C_4)$alkyl, preferably methyl or ethyl, $(C_2-C_6)$alkenyl, preferably $(C_2-C_4)$alkenyl, $(C_2-C_6)$alkynyl, preferably $(C_2-C_4)$alkynyl, $(C_3-C_8)$cycloalkyl, preferably $(C_5-C_6)$cycloalkyl, phenyl, heteroaryl, Hal, preferably F or Cl, —$NO_2$, —CN, —$OR_5$, —$SR_5$, —$SOR_5$, —$SO_2R_5$, —$COR_5$, —$CO_2R_5$, —$CONR_3R_5$, —$SO_2NR_3R_5$, —$NR_3R_5$, —$OCONR_3R_5$, —$NR_3$—$COR_5$, $NR_3$—$CO_2R_5$, or —$NR_3SO_2R_5$, wherein both $R_3$ and $R_5$ are H. In particular embodiments, the compound used is a compound of the general formula I, wherein $R_4$ is absent.

In certain embodiments, the compound used according to the method of the present invention is a compound of the general formula I as defined above, wherein $R_1$ is 3,4,5-trimethoxyphenyl, or 3,4,5-trihydroxyphenyl; $R_3$ is H; and $R_4$ is absent, i.e., a 2-(3,4,5-trimethoxyphenyl)quinazolin-4-amine derivative of the formula Ia or a 5-(4-aminoquinazolin-2-yl)benzene-1,2,3-triol derivative of the formula Ib, respectively (see Table 1). Specific compounds of the general formulas Ia and Ib described herein are herein identified compounds 1-38 in bold (compound 2 is also identified S101, and compound 21 is also identified S145).

TABLE 1

Structures Ia and Ib, indicating 2-(3,4,5-trimethoxyphenyl)quinazolin-4-amine and 5-(4-aminoquinazolin-2-yl)benzene-1,2,3-triol derivatives, respectively

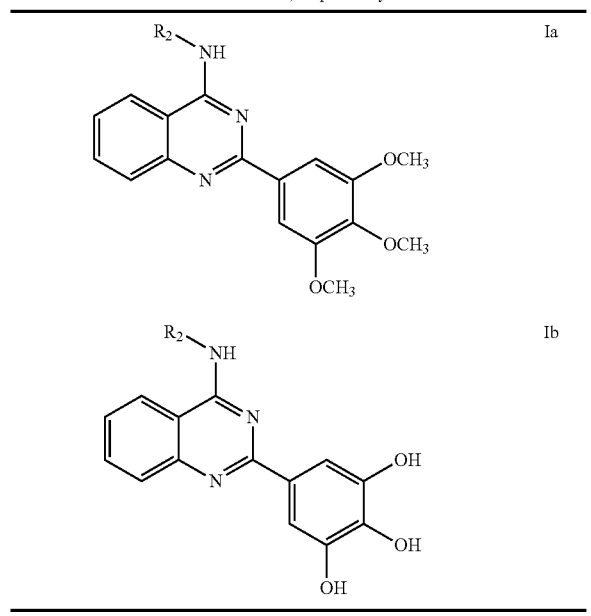

In specific embodiments, the compound used according to the method of the invention is the compound of formula Ia, i.e., a compound of the general formula I in which $R_1$ is 3,4,5-trimethoxyphenyl; $R_3$ is H; and $R_4$ is absent, wherein $R_2$ is phenyl, i.e., N-phenyl-2-(3,4,5-trimethoxyphenyl)quinazolin-4-amine (compound 1); 4-methylphenyl, i.e., N-p-tolyl-2-(3,4,5-trimethoxyphenyl)quinazolin-4-amine (compound 2); 2,4-dimethylphenyl, i.e., N-(2,4-dimethylphenyl)-2-(3,4,5-trimethoxyphenyl)quinazolin-4-amine (compound 3); 4-hydroxyphenyl, i.e., 4-(2-(3,4,5-trimethoxyphenyl)quinazolin-4-ylamino)phenol (compound 4); 4-methoxyphenyl, i.e., N-(4-methoxyphenyl)-2-(3,4,5-trimethoxyphenyl)quinazolin-4-amine (compound 5); 4-octyloxyphenyl, i.e., N-(4-(octyloxy)phenyl)-2-(3,4,5-trimethoxyphenyl)quinazolin-4-amine (compound 6); 4-trifluoromethoxyphenyl, i.e., N-(4-(trifluoromethoxy)phenyl)-2-(3,4,5-trimethoxyphenyl) quinazolin-4-amine (compound 7); 4-chlorophenyl, i.e., N-(4-chlorophenyl)-2-(3,4,5-trimethoxy phenyl)quinazolin-4-amine (compound 8); 2-hydroxymethylphenyl, i.e., (2-(2-(3,4,5-trimethoxyphenyl)quinazolin-4-ylamino)phenyl)methanol (compound 9); benzyl, i.e., N-benzyl-2-(3,4,5-trimethoxyphenyl)quinazolin-4-amine (compound 10); 4-aminobenzyl, i.e., N-(4-aminobenzyl)-2-(3,4,5-trimethoxyphenyl)quinazolin-4-amine (compound 11); 3,4-difluorobenzyl, i.e., N-(3,4-difluorobenzyl)-2-(3,4,5-trimethoxy phenyl)quinazolin-4-amine (compound 12); 3,4-dichlorobenzyl, i.e., N-(3,4-dichlorobenzyl)-2-(3,4,5-trimethoxyphenyl)quinazolin-4-amine (compound 13); 4-methoxybenzyl, i.e., N-(4-methoxybenzyl)-2-(3,4,5-trimethoxy phenyl)quinazolin-4-amine (compound 14); 1H-indazol-6-yl, i.e., N-(1H-indazol-6-yl)-2-(3,4,5-trimethoxyphenyl) quinazolin-4-amine (compound 15); 1H-indazol-5-yl, i.e., N-(1H-indazol-5-yl)-2-(3,4,5-trimethoxyphenyl)quinazolin-4-amine (compound 16); 2-(1H-indol-3-yl)-ethyl, i.e., N-(2-(1H-indol-3-yl)ethyl)-2-(3,4,5-trimethoxyphenyl)quinazolin-4-amine (compound 17); benzo[1,3]dioxol-5-yl, i.e., N-(benzo[d][1,3]dioxol-5-yl)-2-(3,4,5-trimethoxyphenyl) quinazolin-4-amine (compound 18); or 3H-benzoimidazol-5-yl, i.e., N-(3H-benzoimidazol-5-yl)-2-(3,4,5-trimethoxyphenyl)quinazolin-4-amine (compound 19). In a particular specific embodiment, the compound used according to the method of the invention is compound 2, or a pharmaceutically acceptable salt or solvate thereof.

In other specific embodiments, the compound used according to the method of the invention is the compound of formula Ib, i.e., a compound of the general formula I in which $R_1$ is 3,4,5-trihydroxyphenyl; $R_3$ is H; and $R_4$ is absent, wherein $R_2$ is phenyl, i.e., 5-(4-(phenylamino)quinazolin-2-yl)benzene-1,2,3-triol (compound 20), 4-methylphenyl, i.e., 5-(4-(p-tolylamino)quinazolin-2-yl)benzene-1,2,3-triol (compound 21), 2,4-dimethylphenyl, i.e., 5-(4-(2,4-dimethylphenylamino) quinazolin-2-yl)benzene-1,2,3-triol (compound 22), 4-hydroxyphenyl, i.e., 5-(4-(4-hydroxyphenylamino)quinazolin-2-yl)benzene-1,2,3-triol (compound 23), 4-methoxyphenyl, i.e., 5-(4-(4-methoxyphenyl amino)quinazolin-2-yl)benzene-1,2,3-triol (compound 24), 4-octyloxyphenyl, i.e., 5-(4-(4-(octyloxy)phenylamino)quinazolin-2-yl)benzene-1,2,3-triol (compound 25), 4-trifluoro methoxyphenyl, i.e., 5-(4-(4-(trifluoromethoxy)phenylamino)quinazolin-2-yl)benzene-1,2,3-triol (compound 26), 4-chlorophenyl, i.e., 5-(4-(4-chlorophenylamino)quinazolin-2-yl)benzene-1,2,3-triol (compound 27), 2-hydroxymethylphenyl, i.e., 5-(4-(2-(hydroxymethyl)phenylamino)quinazolin-2-yl)benzene-1,2,3-triol (compound 28), benzyl, i.e., 5-(4-(benzylamino) quinazolin-2-yl)benzene-1,2,3-triol (compound 29), 4-aminobenzyl, i.e., 5-(4-(4-aminobenzylamino)quinazolin-2-yl)benzene-1,2,3-triol (compound 30), 3,4-difluorobenzyl, i.e., 5-(4-(3,4-difluorobenzylamino)quinazolin-2-yl)benzene-1,2,3-triol (compound 31), 3,4-dichlorobenzyl, i.e., 5-(4-(3,4-dichlorobenzyl amino)quinazolin-2-yl)benzene-1, 2,3-triol (compound 32), 4-methoxybenzyl, i.e., 5-(4-(4-methoxybenzylamino)quinazolin-2-yl)benzene-1,2,3-triol (compound 33), 1H-indazol-6-yl, i.e., 5-(4-(1H-indazol-6-ylamino)quinazolin-2-yl)benzene-1,2,3-triol (compound 34), 1H-indazol-5-yl, i.e., 5-(4-(1H-indazol-5-ylamino) quinazolin-2-yl)benzene-1,2,3-triol (compound 35), 2-(1H-indol-3-yl)-ethyl, i.e., 5-(4-(2-(1H-indol-3-yl)ethylamino) quinazolin-2-yl)benzene-1,2,3-triol (compound 36), benzo[1,3]dioxol-5-yl, i.e., 5-(4-(benzo[d][1,3]dioxol-5-ylamino) quinazolin-2-yl)benzene-1,2,3-triol (compound 37), or 3H-benzoimidazol-5-yl, i.e., 5-(4-(3H-benzo[d]imidazol-5-ylamino)quinazolin-2-yl)benzene-1,2,3-triol (compound 38).

As found and shown in the Examples section hereinafter, compound 2 is able to effectively penetrate the epidermis/dermis layer of porcine skin, which is an accepted model for human skin.

In another aspect, the present invention thus provides a topical composition comprising a compound of the general formula I as defined above, or a pharmaceutically acceptable salt or solvate thereof, and a pharmaceutically acceptable carrier. In certain embodiments, the topical composition comprises a compound selected from compounds 1-38, herein also identified "the active agent", preferably compound 2, or a pharmaceutically acceptable salt or solvate thereof.

As further shown in the Examples section, all of the compounds of the general formula I that were tested inhibit proliferation of both PBMC and Jurkat cells at micromolar or sub-micromolar concentrations. Compound 2 possesses the highest inhibition potency, with an $IC_{50}$ of 70 nM for the inhibition of PBMC proliferation and 30 nM for the inhibition of Jurkat cell proliferation. Furthermore, 2 only slightly affects the growth of NIH 3T3 (mouse embryonic fibroblasts), A-431 (human vulval carcinoma cells), MDA-MB-468 (human breast carcinoma cells), PANC-1 (human pancreatic carcinoma cells), PC-3 (human prostate cancer), HEK293 (human embryonic kidney), NIH-3T3, A375 (human malignant melanoma), and MDA-MB-231 (human breast adenocarcinoma) and human keratinocytes at high concentrations, at which the growth of Jurkat and PBMC is strongly inhibited. In particular, compound 2 specifically inhibits the proliferation of CD3+ T cells (both CD4+ and CD8+, see Example 7), and has a much lesser effect on the non-T cell fraction of the PBMC. These results suggest that 2 affects cell growth factors that are unique to CD3+ T cells. As shown in Example 8 hereinafter, 2 inhibits proliferating but not non-proliferating CD4+ and CD8+ T cells, thus provides for specific inhibition of the proliferation of adverse T cells directed to allogeneic tissue grafts or auto-antigens.

Compound 2 shows a remarkable ability to inhibit T cell proliferation in a selective manner, as observed in CD3+ cells, PBMC and Jurkat cells. IL-2 is a cytokine secreted in an autocrine manner by T cells to induce their own proliferation. The production of IL-2 determines whether a T cell will proliferate and become an armed effector cell, where the most important function of the co-stimulatory signal is to promote the synthesis of IL-2 [Ka et al., 2006]. The central importance of IL-2 in initiating adaptive immune responses is well illustrated by the drugs that are commonly used to suppress undesirable immune responses. The immunosuppressive drugs cyclosporine A and FK506 (tacrolimus) inhibit IL-2 production by disrupting the signaling through the T cell receptor, whereas rapamycin (sirolimus) inhibits signaling through the IL-2 receptor. Cyclosporine A and rapamycin act synergistically to inhibit immune responses by preventing the IL-2-driven clonal expansion of T cells [Haussmann, 2000; Georgina H. Cornish, 2006]. In experiments described in Example 5 hereinafter, T cells are stimulated using a variety of T cell stimuli. It is a surprising discovery of the present invention that compound 2 does not act by repressing IL-2 secretion. Irrespective of the mode of stimulation, compound 2 has no effect on IL-2 levels in the medium, up to a concentration of 5 µM inhibitor. These findings mean that the dramatic inhibition of proliferation by 2 is caused by a distinct, novel, IL-2 independent mechanism, i.e. a mechanism that does not involve IL-2 secretion.

Thus, in certain embodiments, the treatment of an indication mediated by T cell proliferation is obtained by inhibiting proliferation of T cells without affecting the level of IL-2 secreted from said T cells.

It has further been found in accordance with the present invention that treatment of PBMC and Jurkat cells with 2 led to arrest at the G2 phase of the cell cycle.

The inventors of the present invention also looked for the cellular targets of 2, and found that the compound inhibits the activity of the cytosolic tyrosine kinase ZAP-70, as well as tyrosine phosphorylation of the adaptor protein SLP-76, in a dose-dependent manner, indicating that 2 acts upstream of SLP-76.

T cell proliferation is crucial for development of psoriasis, a common T cell-mediated autoimmune disorder where primary onset of skin lesions is followed by chronic relapses. It is known in the art that the blocking of T cell proliferation led to the inhibition of psoriasis development [Onur Boyman et al., 2004]. Thus, 2 may be useful against graft rejection as well as psoriasis and other inflammatory diseases.

In view of the findings disclosed herein, the topical composition of the present invention is useful for treatment of indications mediated by T cell proliferation. In a preferred embodiment, this composition is used for treatment of psoriasis.

Furthermore, in still another aspect, the present invention provides a compound of the general formula I as defined above, or a pharmaceutically acceptable salt or solvate thereof, for use in treatment of an indication mediated by T cell proliferation.

In certain embodiments, the indication mediated by T cell proliferation is selected from the group consisting of psoriasis, Host-Versus-Graft-Disease (HVGD) and Graft-Versus-Host-Disease (GVHD).

In yet another aspect, the present invention relates to use of a compound of the general formula I as defined above, or a pharmaceutically acceptable salt or solvate thereof, for the preparation of a pharmaceutical composition for treatment of an indication mediated by T cell proliferation.

In a further aspect, the present invention provides a compound of the general formula II as defined above, or a pharmaceutically acceptable salt or solvate thereof, wherein $R_1$ is trimethoxyphenyl, preferably 3,4,5-trimethoxyphenyl, or trihydroxyphenyl, preferably 3,4,5-trihydroxyphenyl; and $R_2$ is phenyl, 4-methylphenyl, 2,4-dimethylphenyl, 4-hydroxyphenyl, 4-methoxyphenyl, 4-octyloxyphenyl, 4-trifluoromethoxyphenyl, 4-chlorophenyl, benzyl, 4-aminobenzyl, 3,4-difluorobenzyl, 3,4-dichlorobenzyl, 4-methoxybenzyl, or 2-hydroxymethylphenyl. In a particular embodiment, the compound of the present invention is a compound of the general formula II, wherein $R_1$ is 3,4,5-trimethoxyphenyl and $R_2$ is 4-methylphenyl (compound 2). The compounds of the general formula II are, in fact, particular examples of the compound of the general formula I.

In still a further aspect, the present invention provides a pharmaceutical composition comprising a compound of the general formula II as defined above, or a pharmaceutically acceptable salt or solvate thereof, and a pharmaceutically acceptable carrier. In certain embodiments, the pharmaceutical composition of the present invention comprises a compound selected from compounds 1-14 and 20-33, preferably compound 2, or a pharmaceutically acceptable salt or solvate thereof.

In certain embodiments, the pharmaceutical compositions are for intravenous, intramuscular, or subcutaneous administration.

In a related aspect, the present invention provides a topical composition comprising a compound of the general formula II as defined above, or a pharmaceutically acceptable salt or solvate thereof, and a pharmaceutically acceptable carrier. In certain embodiments, the topical composition comprises a compound selected from compounds 1-14 and 20-33, preferably compound 2, or a pharmaceutically acceptable salt or solvate thereof, and is preferably used for treatment of psoriasis.

The pharmaceutical compositions comprising a compound of the general formula II are useful for treatment of indications mediated by T cell proliferation, and are in particular useful for IL-2 independent inhibition of T cell proliferation.

In certain embodiments, the compositions of the present invention, i.e., both the topical composition and the pharmaceutical composition, comprise a non-toxic pharmaceutically acceptable salt of the active agent. Suitable pharmaceutically acceptable salts include acid addition salts such as, without being limited to, those formed with hydrochloric acid, fumaric acid, p-toluenesulfonic acid, maleic acid, succinic acid, acetic acid, citric acid, tartaric acid, carbonic acid, or phosphoric acid. Salts of amine groups may also comprise quaternary ammonium salts in which the amino nitrogen atom carries a suitable organic group such as an alkyl, alkenyl, allynyl, or aralkyl moiety. Furthermore, where the compounds of the general formula I or II carry an acidic moiety, suitable pharmaceutically acceptable salts thereof may include metal salts such as alkali metal salts, e.g., sodium or potassium salts, and alkaline earth metal salts, e.g., calcium or magnesium salts.

The pharmaceutically acceptable salts of the present invention may be formed by conventional means, e.g., by reacting the free base form of the active agent with one or more equivalents of the appropriate acid in a solvent or medium in which the salt is insoluble, or in a solvent such as water which is removed in vacuo or by freeze drying, or by exchanging the anions of an existing salt for another anion on a suitable ion exchange resin.

The present invention encompasses solvates of the active agent as well as salts thereof, e.g., hydrates.

The compositions provided by the present invention may be prepared by conventional techniques, e.g., as described in Remington: The Science and Practice of Pharmacy, 19$^{th}$ Ed., 1995. The compositions can be prepared, e.g., by uniformly and intimately bringing the active agent into association with a liquid carrier, a finely divided solid carrier, or both, and then, if necessary, shaping the product into the desired formulation. The compositions may be in liquid, solid or semisolid form and may further include pharmaceutically acceptable fillers, carriers, diluents or adjuvants, and other inert ingredients and excipients.

The compositions can be formulated for any suitable route of administration, but they are preferably formulated for topical administration. Other possible routes of administration are parenteral administration, e.g., intravenous, intraarterial, intramuscular, subcutaneous or intraperitoneal administration. The dosage will depend on the state of the patient, and will be determined as deemed appropriate by the practitioner.

The pharmaceutical compositions of the invention may be in the form of a sterile injectable aqueous or oleagenous suspension, which may be formulated according to the known art using suitable dispersing, wetting or suspending agents. The sterile injectable preparation may also be a sterile injectable solution or suspension in a non-toxic parenterally acceptable diluent or solvent. Acceptable vehicles and solvents that may be employed include, without limiting, water, Ringer's solution and isotonic sodium chloride solution.

The topical composition may be in the form of a lotion or cream and may be administered with other agents for skin treatment. In particular, it has been found in accordance with the present invention that Labrasol® is an efficient carrier that enables penetration of the compounds of the present invention into the epidermis/dermis layer.

The compounds used according to the method of the present invention may be synthesized according to any technology or procedure known in the art. A particular procedure for the preparation of the compounds of the general formula II is provided in detail in the Examples section hereinafter.

The invention will now be illustrated by the following non-limiting examples.

EXAMPLES

Materials and Methods

Chemistry.

Thin-layer chromatography was carried out on Merck aluminum sheets, silica gel 60 F254 and visualized with UV light at 254 nm. Preparative column chromatography was performed on Merck silica gel 60 (70-230 mesh). High-pressure liquid chromatography (HPLC) was performed on a Merck Hitachi HPLC, which included an L 6200 pump, a D 6000A interphase, L-4250 UV detector and AS-4000 autosampler. Integration employed the HSM HPLC System Manager, Merck KgaA, Darmstadt and Hitachi Instruments, Inc., San Jose. Reversed-phase preparative HPLC was performed with a C-18 column (218TPL022 Vydac).

Mass spectrometry was performed using an LCQDUO, from ThermoQuest of Finnigan, and NMR was on a Bruker AMX 300. Chemical shifts δ are given in ppm referring to the signal center using the solvent peaks for reference: CDCl3 7.26/77.0 ppm and DMSO-d6 2.49/39.7 ppm.

Combustion elemental analysis was performed using a PerkinElmer 2400 Elemental Analyzer.

All solvents for HPLC analysis and purification were purchased from J. T. Baker, BDH or Bio-Lab Ltd. (Israel). Reagents for chemical synthesis were from Frutarom Acros (Geel, Belgium), Fluka (Taufkirchen, Germany), or Sigma-Aldrich (Steinheim, Germany).

Melting point (m.p.) was determined using a Fisher-John melting point apparatus (Fisher Scientific).

Synthesis.

p-Tolyamine.

4-Nitrotoluene (7.95 g, 5.8 mmol) in a solution of EtOH:H$_2$O 9:1 (8 ml) was added dropwise to a mixture of hydrazine hydrate and Raney Nickel (7 ml, 14.4 mol) in aq. ethanol (10 ml) at 60° C. After reflux was attained, an additional quantity of hydrazine hydrate (2 ml) was added. The mixture was left to reflux for 25 min, cooled to room temperature, filtered and evaporated to afford p-tolyamine (5.2 g, 0.048 mol, 84%). m.p.: 52-53° C.; $^1$H NMR (300 MHz, DMSO-d$_6$) δ 6.27 (s, 2H), 6.63 (d, J=5.9 Hz, 2H), 6.81 (t, J=7 Hz, 1H), 7.20 (t, J=7 Hz, 2H).

2,4-Dichloroquinazoline [Nagarathnam Dhanapalan, 2002]:

POCl$_3$ (40 ml) was stirred at room temperature for 20 min and was then added to a flask containing 2,4-quinolinedione (10 g, 0.06 mol). The mixture was heated to reflux for 48 h. The brown solution was cooled to 50° C., poured into cold water (0° C., 40 ml) while stirring vigorously. The aqueous mixture was maintained at a temperature below 30° C. during the quench. The cold precipitate was filtered, washed with cold water (3×60 ml) and dried under high vacuum to afford 8 g (0.04 mol) of 2,4-dichloroquinazoline (71%). m.p.: 118° C.; $^1$H NMR (300 MHz, DMSO-d$_6$) δ 7.58 (t, J=7.6 Hz, 1H), 7.84 (t, J=6.5 Hz, 2H), 8.16 (d, J=6.9 Hz, H).

(2-Chloro-quinazolin-4-yl)-p-tolyl-amine [Nagarathnam Dhanapalan, 2002]:

A mixture of 2,4-dichloroquinazoline (5.8 g, 0.029 mol), p-tolyamine (3.5 g, 0.032 mol), and potassium acetate (3.72 g, 0.038 mol) in THF/water (66 ml/30 ml) was stirred at room temperature for 16 h. Water (66 ml) was added to the mixture, and a precipitate was formed. The precipitate was washed with water, filtered, and dried under high vacuum to afford (2-chloro-quinazolin-4-yl)-p-tolyl-amine (5.65 g, 0.021 mol, 70%). m.p.: 198-199° C.; $^1$H NMR (300 MHz, DMSO-d$_6$) δ 2.27 (s, 3H), 7.21 (d, J=7.8 Hz, 2H), 7.50 (d, J=7.2 Hz, 3H), 7.83 (t, J=8.5 Hz, 2H), 8.50 (t, J=8.0 Hz, 1H).

p-Tolyl-[2-(3,4,5-trimethoxy-phenyl)-quinazolin-4-yl]-amine, 2, Synthesis:

A mixture of (2-chloro-quinazolin-4-yl)-p-tolyl-amine, 3.76 g, 0.014 mol), ethylene-glycol-dimethyl-ether/water (1 l/120 ml), 3,4,5-trimethoxyphenylboronic acid (2.714 g, 0.014 mol) and sodium bicarbonate (3.6 g) was degassed with argon for 15 minutes. Pd(dppf)Cl$_2$ (0.84 g) was added, and the mixture was heated to reflux overnight. After cooling to room temperature CH$_2$Cl$_2$ (1 l) and H$_2$O (500 ml) were added. The organic and aqueous layers were separated, the aqueous layer was extracted with CH$_2$Cl$_2$ (2×500 ml), and the combined organic layers were dried over anhydrous sodium sulfate. The organic solvent was removed under reduced pressure. The crude product was purified by methanol. Filtration in a Büchner apparatus afforded p-tolyl-[2-(3,4,5-trimethoxy-phenyl)-quinazolin-4-yl]-amine, 2 (3.15 g, 0.0078 mol 56%). m.p.: >250° C.; $^1$H NMR (300 MHz, DMSO-d$_6$) δ 2.33 (s, 3H), 3.74 (s, 3H), 3.91 (s, 6H), 6.81 (s, 2H), 7.24 (d, J=8.4 Hz, 2H), 7.33 (d, J=7.3 Hz, 2H), 7.58 (t, J=8.2 Hz, 1H), 7.83 (t, J=7.2 Hz, 2H), 8.54 (d, J=7.5 Hz, 1H). Anal. (C$_{24}$H$_{23}$N$_3$O$_3$) C, H, N.

p-Tolyl-[2-(3,4,5-trimethoxyphenyl)-quinazolin-4-yl]-amine methanesulfonic salt, 2 mesylate:

p-Tolyl-([2-(3,4,5-trimethoxyphenyl)-quinazolin-4-yl]-amine (2, 100 mg 0.25 mmol) was dissolved in THF at room temperature, and methanesulfonic acid (1.2 eq. 20 µl, 0.3 mmol) was added to the mixture. The mixture was mixed at room temperature until a precipitate was observed. The THF was decanted and the precipitate was washed 3 times with 3 ml of diethyl ether, the ether was removed and the precipitate was dried under nitrogen stream to afford yellow crystals of p-tolyl-[2-(3,4,5-trimethoxy-phenyl)-quinazolin-4-yl]-amine methanesulfonic salt (119 mg, 0.24 mmol, 96%). m.p.>250° C.; $^1$H NMR (300 MHz, DMSO-d$_6$) δ 2.33 (s, 3H), 3.74 (s, 3H), 3.91 (s, 6H), 6.81 (s, 2H), 7.24 (d, J=7.7 Hz, 2H), 7.33 (d, J=6.7 Hz, 2H), 7.58 (t, J=7.1 Hz, 1H), 7.83 (t, J=7.8 Hz, 2H), 8.54 (d, J=8.0 Hz, 1H).

Demethylation of 2: 5-(4-(p-tolylamino)quinazolin-2-yl) benzene-1,2,3-triol, 21:

An aryl methoxy derivative p-tolyl-[2-(3,4,5-trimethoxy-phenyl)-quinazolin-4-yl]-amine (2, 30 mg, 7.5e-5 mol) was dissolved in anhydrous DCM (minimal volume, not fully dissolved); the round flask was then sealed. BBr$_3$ (76 µl, 0.111 gr, 205 gr/mol, d=1.45, 2 equiv/per methoxy group, here 6 eq. were used 5.5e-4 mol) was added drop wise (from a syringe) and the reaction mixture was stirred at room temperature for 1 h. The degree of conversion was monitored by HPLC until full conversion was achieved, and the reaction was then quenched with methanol and evaporated to low volume. Another wash was performed using methanol, followed by a wash with acetonitrile and evaporation, to obtain 5-(4-(p-tolylamino)quinazolin-2-yl)benzene-1,2,3-triol, 21 (24 mg, 6.6e-5 mol, 90%). m.p>250° C.; $^1$H NMR (300 MHz, DMSO-d$_6$) δ 2.35 (s, 3H), 6.75 (s, 2H), 7.22 (d, J=8.0 Hz, 2H), 7.35 (d, J=7.5 Hz, 2H), 7.56 (t, J=8.0 Hz, H), 7.82 (t, J=8.2 Hz, 2H), 8.24 (d, J=7.5 Hz, 1H). Anal. (C$_{21}$H$_{17}$N$_3$O$_3$) C, H, N.

$^1$H NMR and Elemental Analysis of Compounds 1, 3-20, 22-38:

N-phenyl-2-(3,4,5-trimethoxyphenyl)quinazolin-4-amine, 1. m.p.>250° C.; $^1$H NMR (300 MHz, DMSO-d$_6$) δ 3.83 (s, 9H), 6.81 (s, 3H), 7.20 (t, J=7.8 Hz, 2H), 7.58-7.67 (m, 3H), 7.85 (d, J=8.0 Hz, 2H), 8.16 (d, J=8.4 Hz, 1H). Anal. (C$_{23}$H$_{21}$N$_3$O$_3$) C, H, N.

N-(2,4-dimethylphenyl)-2-(3,4,5-trimethoxyphenyl) quinazolin-4-amine, 3. m.p.>250° C.; $^1$H NMR (300 MHz, DMSO-d$_6$) δ 2.14 (s, 3H), 2.37 (s, 3H), 3.83 (s, 9H), 6.48 (d, J=7.0 Hz, 1H), 6.76-6.85 (m, 4H), 7.60 (t, J=8.9 Hz, 1H), 7.85 (t, J=7.2 Hz, 2H), 8.21 (d, J=7.3 Hz, 1H). Anal. (C$_{25}$H$_{25}$N$_3$O$_3$) C, H, N.

4-(2-(3,4,5-trimethoxyphenyl)quinazolin-4-ylamino)phenol, 4. m.p.>250° C.; $^1$H NMR (300 MHz, DMSO-d$_6$) δ 3.83 (s, 9H), 6.70 (d, J=7.0 Hz, 2H), 6.83 (s, 2H), 7.21 (d, J=6.8 Hz, 2H), 7.56 (t, J=7.1 Hz, 1H), 7.86 (t, J=7.1 Hz, 2H), 8.13 (d, J=7.0 Hz, 1H). Anal. (C$_{23}$H$_{21}$N$_3$O$_4$) C, H, N.

N-(4-methoxyphenyl)-2-(3,4,5-trimethoxyphenyl) quinazolin-4-amine, 5. m.p.>250° C.; $^1$H NMR (300 MHz, DMSO-d$_6$) δ 3.85 (s, 10H), 4.35 (s, 2H), 6.79 (s, 2H), 6.89 (d, J=6.9 Hz, 2H), 7.27 (d, J=7.0 Hz, 2H), 7.56 (t, J=7.1 Hz, 1H), 7.84 (t, J=7.1 Hz, 2H), 8.13 (d, J=7.0 Hz, 1H). Anal. (C$_{24}$H$_{23}$N$_3$O$_4$) C, H, N.

N-(4-(octyloxy)phenyl)-2-(3,4,5-trimethoxyphenyl) quinazolin-4-amine, 6. m.p.>250° C.; $^1$H NMR (300 MHz, DMSO-d$_6$) δ 0.90 (t, J=8.2 Hz, 3H), 1.29-1.43 (m, 10H), 1.78 (q, J=8.6 Hz, 2H), 3.83 (s, 9H), 4.06 (t, J=8.3 Hz, 2H), 6.74 (d, J=6.9 Hz, 2H), 6.81 (s, 2H), 7.55-7.60 (m, 3H), 7.84 (t, J=8.1 Hz, 2H), 8.19 (d, J=7.0 Hz, 1H). Anal. (C$_{24}$H$_{23}$N$_3$O$_3$) C, H, N.

N-(4-(trifluoromethoxy)phenyl)-2-(3,4,5-trimethoxyphenyl) quinazolin-4-amine, 7. m.p.>250° C.; $^1$H NMR (300 MHz, DMSO-d$_6$) δ 3.83 (s, 9H), 6.74 (d, J=6.9 Hz, 2H), 6.86 (s, 2H), 7.56 (dd, J=8.3 Hz 3H), 7.84 (t, J=7.0 Hz, 2H), 8.16 (d, J=6.9 Hz, 1H). Anal. (C$_{24}$H$_{20}$F$_3$N$_3$O$_4$) C, H, N.

N-(4-chlorophenyl)-2-(3,4,5-trimethoxy phenyl)quinazolin-4-amine, 8. m.p.>250° C.; $^1$H NMR (300 MHz, DMSO-d$_6$) δ 3.83 (s, 9H), 6.83 (s, 2H), 7.21 (d, J=6.8 Hz, 2H), 7.57 (t, J=7.1 Hz, 1H), 7.84 (t, J=7.1 Hz, 2H), 8.13 (d, J=7.0 Hz, 1H). Anal. (C$_{23}$H$_{20}$ClN$_3$O$_3$) C, H, N.

(2-(2-(3,4,5-trimethoxyphenyl)quinazolin-4-ylamino) phenyl)methanol, 9. m.p.>250° C.; $^1$H NMR (300 MHz, DMSO-d$_6$) δ 3.79 (s, 9H), 4.61 (s, 2H), 6.54 (d, J=7.0 Hz, 1H), 6.70 (t, J=7.1 Hz, 1H), 6.89 (s, 2H), 7.11 (t, J=7.8 Hz, 2H), 7.59 (t, J=8.5 Hz, 1H), 7.86 (t, J=8.1 Hz, 2H), 8.16 (d, J=7.0 Hz, 1H). Anal. (C$_{24}$H$_{23}$N$_3$O$_4$) C, H, N.

N-benzyl-2-(3,4,5-trimethoxyphenyl)quinazolin-4-amine, 10. m.p.>250° C.; $^1$H NMR (300 MHz, DMSO-d$_6$) δ 3.83 (s, 9H), 4.36 (s, 2H), 6.84 (s, 2H), 7.23-7.33 (m, 5H), 7.56 (t, J=7.1 Hz, 1H), 7.84 (t, J=8.1 Hz, 2H), 8.13 (d, J=7.5 Hz, 2H). Anal. (C$_{24}$H$_{23}$N$_3$O$_3$) C, H, N.

N-(4-aminobenzyl)-2-(3,4,5-trimethoxyphenyl)quinazolin-4-amine, 11. m.p.>250° C.; $^1$H NMR (300 MHz, DMSO-d$_6$) δ 2.34 (s, 3H), 4.35 (s, 2H), 6.81 (s, 2H), 7.11 (d, J=6.8 Hz, 4H), 7.58 (t, J=7.4 Hz, 1H), 7.89 (t, J=7.1 Hz, 2H), 8.18 (d, J=7.8 Hz, 1H). Anal. (C$_{24}$H$_{24}$N$_4$O$_3$) C, H, N.

N-(3,4-difluorobenzyl)-2-(3,4,5-trimethoxyphenyl) quinazolin-4-amine, 12. m.p.>250° C.; $^1$H NMR (300 MHz, DMSO-d$_6$) δ 3.86 (s, 9H), 4.38 (s, 2H), 6.68-6.75 (m, 1H), 7.12-7.18 (m, 2H), 7.56 (t, J=7.1 Hz, 1H), 7.84 (t, J=7.1 Hz, 2H), 8.13 (d, J=7.0 Hz, 1H). Anal. (C$_{24}$H$_{21}$F2N$_3$O$_3$) C, H, N.

N-(3,4-dichlorobenzyl)-2-(3,4,5-trimethoxyphenyl) quinazolin-4-amine, 13. m.p.>250° C.; $^1$H NMR (300 MHz, DMSO-d$_6$) δ 3.82 (s, 9H), 4.40 (s, 2H), 6.81 (s, 2H), 7.20 (d, J=7.0 Hz, H), 7.37 (s, 1H), 7.58-7.64 (m, 2H), 7.60 (t, J=7.2 Hz, 1H), 7.83 (t, J=7.2 Hz 1H) 8.15 (d, J=7.5 Hz, 1H). Anal. (C$_{24}$H$_{21}$C$_{12}$N$_3$O$_3$) C, H, N.

N-(4-methoxybenzyl)-2-(3,4,5-trimethoxyphenyl) quinazolin-4-amine, 14. m.p.>250° C.; $^1$H NMR (300 MHz, DMSO-d$_6$) δ 3.87 (s, 10H), 4.35 (s, 2H), 6.81 (s, 2H), 6.89 (d, J=7.5 Hz, 2H), 7.25 (d, J=7.6 Hz, 2H), 7.60 (t, J=8.2 Hz, 1H), 7.83-7.90 (m, 2H) 8.21 (d, J=6.9 Hz, 1H). Anal. (C$_{25}$H$_{25}$N$_3$O$_3$) C, H, N.

N-(1H-indazol-6-yl)-2-(3,4,5-trimethoxyphenyl) quinazolin-4-amine, 15. m.p.>250° C.; $^1$H NMR (300 MHz, DMSO-d$_6$) δ 3.83 (s, 9H), 6.58 (d, J=7.0 Hz, 1H), 6.81 (S, 2H), 7.05 (s, 1H), 7.56 (t, J=7.1 Hz, 1H), 7.84 (t, J=7.1 Hz, 2H), 8.07 (d, J=7.1 Hz, 2H), 8.07 (d, J=7.0 Hz, 1H), 8.16 (d, J=7.0 Hz, 1H). Anal. (C$_{24}$H$_{21}$N$_5$O$_3$) C, H, N.

N-(1H-indazol-5-yl)-2-(3,4,5-trimethoxyphenyl)quinazolin-4-amine, 16. m.p.>250° C.; NMR (300 MHz, DMSO-d$_6$) δ 3.83 (s, 9H), 6.54 (d, J=7.0 Hz, 1H), 6.81 (S, 2H), 7.06 (s, 1H), 7.56 (t, J=7.1 Hz, 1H), 7.84 (t, J=7.1 Hz, 2H), 8.08 (d, J=7.1 Hz, 2H), 8.16 (d, J=7.0 Hz, 1H) 8.21 (t, J=7.1 Hz, 1H). Anal. (C$_{24}$H$_{21}$N$_5$O$_3$) C, H, N.

N-(2-(1H-indol-3-yl)ethyl)-2-(3,4,5-trimethoxyphenyl)quinazolin-4-amine, 17. m.p.>250° C.; $^1$H NMR (300 MHz, DMSO-d$_6$) δ 2.68 (t, J=7.1 Hz 2H), 3.34 (t, J=7.1 Hz 2H), 3.85 (s, 9H), 6.80 (s, 2H), 7.13-7.19 (m, 2H), 7.34-7.38 (m, 1H), 7.49 (s, 1H), 7.58-7.67 (m, 2H), 7.83-7.89 (m, 2H), 8.16 (d, J=7.0 Hz, 1H). Anal. (C$_{27}$H$_{26}$N$_4$O$_3$) C, H, N.

N-(benzo[d][1,3]dioxol-5-yl)-2-(3,4,5-trimethoxyphenyl)quinazolin-4-amine, 18. m.p.>250° C.; $^1$H NMR (300 MHz, DMSO-d$_6$) δ 3.80 (s, 9H), 6.10 (s, 2H), 6.67 (d, J=6.8 Hz, 1H), 6.83 (s, 2H), 7.11 (d, J=7.8 Hz, 1H), 7.54-7.59 (m, 2H), 7.85 (t, J=7.1 Hz, 1H), 8.18 (d, J=7.6 Hz, 1H). Anal. (C$_{24}$H$_{21}$N$_3$O$_5$) C, H, N.

N-(3H-benzoimidazol-5-yl)-2-(3,4,5-trimethoxyphenyl) quinazolin-4-amine, 19. m.p.>250° C.; $^1$H NMR (300 MHz, DMSO-d$_6$) δ 3.86 (s, 9H), 6.48 (d, J=7.0 Hz, 1H), 6.83 (S, 2H), 6.90 (s, 1H), 7.36 (d, J=6.9 Hz, 1H), 7.58 (t, J=8.1 Hz, 1H), 7.85 (t, J=7.1 Hz, 2H), 8.16 (d, J=8.0 Hz, 1H). Anal. (C$_{24}$H$_{21}$N$_5$O$_3$) C, H, N.

5-(4-(phenylamino)quinazolin-2-yl)benzene-1,2,3-triol, 20. m.p.>250° C.; $^1$H NMR (300 MHz, DMSO-d$_6$) δ 5.42 (s, 3H), 6.71 (s, 2H), 6.89 (t, J=6.9 Hz, 1H), 7.24 (t, J=7.0 Hz 2H), 7.58-7.69 (m, 3H), 7.87 (t, J=7.1 Hz, 1H), 8.23 (d, J=6.9 Hz, 1H). Anal. (C$_{20}$H$_{15}$N$_3$O$_3$) C, H, N.

5-(4-(2,4-dimethylphenylamino)quinazolin-2-yl)benzene-1,2,3-triol, 22. m.p.>250° C.; $^1$H NMR (300 MHz, DMSO-d$_6$) δ 2.11 (s, 3H), 2.38 (s, 3H), 6.38 (d, J=7.7 Hz, 1H), 6.70 (s, 2H), 6.76 (d, J=7.4 Hz, 1H), 6.85 (m, H), 7.58 (t, J=8.9 Hz, 1H), 7.85 (t, J=7.2 Hz, 2H), 8.15 (d, J=7.3 Hz, 1H). Anal. (C$_{22}$H$_{19}$N$_3$O$_3$) C, H, N.

5-(4-(4-hydroxyphenylamino)quinazolin-2-yl)benzene-1, 2,3-triol, 23. m.p.>250° C.; $^1$H NMR (300 MHz, DMSO-d$_6$) δ 5.37 (s, 3H), 6.72 (t, J=7.1 Hz, 4H), 6.86 (s, 2H), 7.23 (d, J=8.8 Hz, 2H), 7.56 (t, J=8.1 Hz, 1H), 7.86 (t, J=7.1 Hz, 2H), 8.13 (d, J=8.0 Hz, 1H). Anal. (C$_{19}$H$_{14}$N$_3$O$_4$) C, H, N.

5-(4-(4-methoxyphenyl amino)quinazolin-2-yl)benzene-1,2,3-triol, 24. m.p.>250° C.; $^1$H NMR (300 MHz, DMSO-d$_6$) δ 3.86 (s, 1H), 5.35 (s, 3H), 6.74 (s, 2H), 6.84 (d, J=7.8 Hz, 2H), 7.23 (d, J=6.9 Hz, 2H), 7.57 (t, J=8.1 Hz, 1H), 7.84 (t, J=7.1 Hz, 2H), 8.13 (d, J=7.0 Hz, 1H). Anal. (C$_{21}$H$_{17}$N$_3$O$_4$) C, H, N.

5-(4-(4-(octyloxy)phenylamino)quinazolin-2-yl)benzene-1,2,3-triol, 25. m.p.>250° C.; $^1$H NMR (300 MHz, DMSO-d$_6$) δ 0.88 (t, J=8.0 Hz, 3H), 1.31-1.46 (m, 10H), 1.78 (q, J=8.5 Hz, 2H), 4.00 (t, J=8.0 Hz, 2H), 6.70 (d, J=7.5 Hz, 2H), 6.80 (s, 2H), 7.54-7.64 (m, 3H), 7.84 (t, J=8.0 Hz, 2H), 8.13 (d, J=7.0 Hz, 1H). Anal. (C$_{28}$H$_{31}$N$_3$O$_4$) C, H, N.

5-(4-(4-(trifluoromethoxy)phenylamino)quinazolin-2-yl) benzene-1,2,3-triol, 26. m.p.>250° C.; $^1$H NMR (300 MHz, DMSO-d$_6$) δ 5.32 (s, 3H), 6.71 (s, 2H), 6.77 (d, J=6.9 Hz 2H), 7.55 (dd, J=7.3 Hz 3H), 7.84 (t, J=8.0 Hz, 2H), 8.16 (d, J=7.9 Hz, 1H). Anal. (C$_{21}$H$_{14}$F3N$_3$O$_4$) C, H, N.

5-(4-(4-chlorophenylamino)quinazolin-2-yl)benzene-1,2, 3-triol, 27. m.p.>250° C.; $^1$H NMR (300 MHz, DMSO-d$_6$) δ 5.33 (s, 3H), 6.69 (s, 2H), 7.23 (d, J=6.8 Hz, 2H), 7.56 (t, J=7.1 Hz, 1H), 7.86 (t, J=7.1 Hz, 2H), 8.13 (d, J=7.0 Hz, 1H). Anal. (C$_{20}$H$_{14}$ClN$_3$O$_3$) C, H, N.

5-(4-(2-(hydroxymethyl)phenylamino)quinazolin-2-yl) benzene-1,2,3-triol, 28. m.p.>250° C.; $^1$H NMR (300 MHz, DMSO-d$_6$) δ 5.35 (s, 3H), 4.59 (s, 2H), 6.58 (d, J=7.0 Hz, 1H), 6.80 (t, J=7.1 Hz, 1H), 6.91 (s, 2H), 7.12 (t, J=7.1 Hz, 2sH), 7.59 (t, J=7.1 Hz, 1H), 7.86 (t, J=7.1 Hz, 2H), 8.16 (d, J=7.0 Hz, 1H). Anal. (C$_{21}$H$_{17}$N$_3$O$_4$) C, H, N.

5-(4-(benzylamino)quinazolin-2-yl)benzene-1,2,3-triol, 29. m.p>250° C.; $^1$H NMR (300 MHz, DMSO-d$_6$) δ 4.24 (s, 2H), 6.58 (s, 2H), 7.18-7.27 (m, 5H), 7.55 (t, J=8.2 Hz, 1H), 7.84 (t, J=8.6 Hz, 2H), 8.12 (d, J=7.0 Hz, 1H). Anal. (C$_{21}$H$_{17}$N$_3$O$_3$) C, H, N.

5-(4-(4-aminobenzylamino)quinazolin-2-yl)benzene-1,2, 3-triol, 30. m.p.>250° C.; $^1$H NMR (300 MHz, DMSO-d$_6$) δ 2.34 (s, 3H), 4.35 (s, 2H), 5.35 (s, 3H), 7.11 (d, J=6.8 Hz, 4H), 7.58 (t, J=7.1 Hz, 1H), 7.87 (t, J=7.1 Hz, 2H), 8.23 (d, J=7.0 Hz, 1H). Anal. (C$_{21}$H$_{18}$N$_4$O$_3$) C, H, N.

5-(4-(3,4-difluorobenzylamino)quinazolin-2-yl)benzene-1,2,3-triol, 31. m.p.>250° C.; $^1$H NMR (300 MHz, DMSO-d$_6$) δ 4.36 (s, 2H), 5.35 (s, 3H), 6.70 (s, 2H), 6.74-6.79 (m, 1H), 7.10-7.19 (m, 2H), 7.57 (t, J=7.1 Hz, 1H), 7.84 (t, J=7.1 Hz, 2H), 8.13 (d, J=7.0 Hz, 1H). Anal. (C$_{21}$H$_{15}$F$_2$N$_3$O$_3$) C, H, N.

5-(4-(3,4-dichlorobenzyl amino)quinazolin-2-yl)benzene-1,2,3-triol, 32. m.p.>250° C.; $^1$H NMR (300 MHz, DMSO-d$_6$) δ 4.34 (s, 2H), 6.78 (s, 2H), 7.22 (d, J=7.6 Hz, 1H), 7.40 (s, 1H), 7.55-7.63 (m, 2H), 7.62 (t, J=7.3 Hz, 1H), 7.82 (t, J=7.0 Hz, 1H) 8.14 (d, J=8.0 Hz, 1H). Anal. (C$_{21}$H$_{15}$Cl$_2$N$_3$O$_3$) C, H, N.

5-(4-(4-methoxybenzylamino)quinazolin-2-yl)benzene-1,2,3-triol, 33. m.p.>250° C.; $^1$H NMR (300 MHz, DMSO-d$_6$) δ 3.83 (s,3H), 4.31 (s, 2H), 6.69 (s, 2H), 6.89 (d, J=7.5 Hz, 2H), 7.31 (d, J=7.0 Hz, 2H), 7.60 (t, J=8.2 Hz, 1H), 7.80-7.93 (m, 2H) 8.21 (d, J=6.9 Hz, 1H). Anal. (C$_{22}$H$_{19}$N$_3$O$_4$) C, H, N.

5-(4-(1H-indazol-6-ylamino)quinazolin-2-yl)benzene-1, 2,3-triol, 34. m.p.>250° C.; $^1$H NMR (300 MHz, DMSO-d$_6$) δ 5.35 (s, 3H), 6.56 (d, J=7.0 Hz, 1H), 6.81 (S, 2H), 7.05 (s, 1H), 7.56 (t, J=7.1 Hz, 1H), 7.84 (t, J=7.1 Hz, 2H), 8.07 (d, J=7.0 Hz, 1H), 8.16 (d, J=7.0 Hz, 1H). Anal. (C$_{23}$H$_{15}$N$_5$O$_3$) C, H, N.

5-(4-(1H-indazol-5-ylamino)quinazolin-2-yl)benzene-1, 2,3-triol, 35. m.p.>250° C.; $^1$H NMR (300 MHz, DMSO-d$_6$) δ 5.36 (s, 3H), 6.56 (d, J=7.0 Hz, 1H), 6.71 (S, 2H), 7.05 (s, 1H), 7.56 (t, J=7.1 Hz, 1H), 7.84 (t, J=7.1 Hz, 2H), 8.08 (d, J=7.1, 2H), 8.16 (d, J=7.0 Hz, 1H) 8.21 (t, J=7.1 Hz, 1H). Anal. (C$_{21}$H$_{15}$N$_5$O$_3$) C, H, N.

5-(4-(2-(1H-indol-3-yl)ethylamino)quinazolin-2-yl)benzene-1,2,3-triol, 36. m.p.>250° C.; $^1$H NMR (300 MHz, DMSO-$d_6$) δ 2.68 (t, J=8.1 Hz 2H), 3.34 (t, J=7.1 Hz 2H), 5.32 (s, 3H), 6.72 (s, 2H), 7.13-7.16 (m, 2H), 7.34-7.38 (m, 1H), 7.44 (s, H), 7.58-7.67 (m, 2H), 7.83-7.87 (m, 2H), 8.16 (d, J=7.8 Hz, 1H). Anal. ($C_{24}H_{20}N_4O_3$) C, H, N.

5-(4-(benzo[d][1,3]dioxol-5-ylamino)quinazolin-2-yl)benzene-1,2,3-triol, 37. m.p.>250° C.; $^1$H NMR (300 MHz, DMSO-$d_6$) δ 5.38 (s, 3H), 6.12 (s, 2H), 6.63 (d, J=6.8 Hz, 1H), 6.78 (s, 2H), 7.11 (d, J=6.8 Hz, 1H), 7.58 (t, J=7.0 Hz, 1H), 7.85 (t, J=7.1 Hz, 2H), 8.18 (d, J=7.0 Hz, 1H). Anal. ($C_{21}H_{15}N_3O_5$) C, H, N.

5-(4-(3H-benzo[d]imidazol-5-ylamino)quinazolin-2-yl)benzene-1,2,3-triol, 38. m.p.>250° C.; $^1$H NMR (300 MHz, DMSO-$d_6$) δ 6.50 (d, J=8.0 Hz, 1H), 6.71 (S, 2H), 6.91 (s, 1H), 7.43 (d, J=7.7 Hz, 1H), 7.63 (t, J=8.0 Hz, 1H), 7.82 (t, J=8.1 Hz, 2H), 8.16 (d, J=8.0 Hz, 1H). Anal. ($C_{21}H_{15}N_5O_3$) C, H, N.

Biology

Culture Conditions.

Jurkat cells (human, acute T cell leukemia line) and human peripheral blood mononuclear cells (PBMC) were grown in RPM1 medium supplemented with 100 U/ml penicillin, 100 microg/ml streptomycin. All cultures were incubated in a humidified incubator at 37° C. in 5% $CO_2$.

NIH 3T3 (mouse embryo fibroblasts), A-431 (human epithelial-like skin carcinoma cells), MDA-MB-468 (human epithelial-like breast carcinoma), PANC-1 (human epithelial-like pancreatic carcinoma), PC-3 (human prostate cancer cells), HEK293 (human embryonic kidney cells), A375 (human malignant melanoma), were grown in DMEM medium (Biological Industries, Beit Haemek), supplemented with 100 U/ml penicillin, 100 mg/ml streptomycin. MDA-MB-231 (human breast adenocarcinoma) were grown with Leibovitz's L-15 Medium (Biological Industries, Beit Haemek), supplemented with 100 U/ml penicillin, 100 mg/ml streptomycin.

Primary human keratinocytes were maintained in keratinocyte growth medium (KGM): DMEM, 25% Nutrient mixture F-12 (HAM), 10% fetal bovine serum, 5 µg/ml insulin, 0.4 µg/ml hydrocortisone, 0.1 nM cholera toxin, 10 ng/ml epidermal growth factor, $1.8×10^{-4}$ M adenine, 5 µg/ml transferrin, 2 nM T3, 100,000 U/l penicillin, 100 µg/l streptomycin, 0.1 mg/ml amphotericin. The primary keratinocytes were cultured from small biopsy specimens.

T Cell Isolation and Stimulation.

Blood samples were taken from healthy donors and loaded on a Ficoll density gradient to purify the PBMC population. T cells were purified by human anti-CD3 using an autoMACS instrument (Miltenyi Biotec, Bergisch-Gladbach, Germany), according to the manufacturer's instructions. The identity of T cells was confirmed by flow cytometry, as they stained positive for CD3. Cells were stimulated with ConA (10 µg/ml), ODN2006 (0.5 µg/ml; Enzo Life Sciences), or LPS (50 µg/ml; Sigma-Aldrich, Steinheim, Germany), for 72 h in the presence of the inhibitor, and their proliferation was measured in the BrdU incorporation assay as will be later described.

Antibodies.

Antibodies used in this study were: Hybridoma C305, specific for the Jurkat Ti beta chain of TCR (from Dr. D. Yablonski, Technion, Israel); anti-ZAP-70 (05-253) from Upstate Biotechnology (Lake Placid, N.Y.); anti-SLP-76 (sc-9062) from Santa Cruz Biotech (Santa Cruz, Calif.); Hybridoma 4G-10 specific for phosphorylated tyrosine (from our collection); anti-CD28 (MCA709XZ) from Serotec (Cergy Saint-Christophe, France); anti-PG SK3 (9331) and anti-Glyceraldehyde-3-phosphate dehydrogenase (GAPDH) (2118) from Cell Signaling Technology (Beverly, Mass.).

DNA 5-bromo 2'-deoxyuridine (BrdU) Incorporation Assay.

Cells were depleted of fetal calf serum (FCS) for 12 hours. They were then stimulated to proliferate by addition of ConA (10 µg/ml) for PBMC from healthy individuals and for Jurkat cells, FCS (10%) for HEK293 and A375 cells, PDGF (30 ng/ml) for NIH 3T3 cells, and EGF (30 ng/ml) for MDA-MB-231, Cells ($1×10^5$) were cultured in 96-well plates for 3 days in the presence or absence of inhibitors at the concentrations specified in the text. Each condition was tested in duplicate wells.

Proliferation was assessed by BrdU incorporation using a colorimetric ELISA kit (Roche, Germany). Subsequent to labeling with 10 µM BrdU, DNA was denatured and the cells were incubated with anti-BrdU-POD, prior to the addition of colorimetric substrate (TMB). The reaction product was quantified by measuring absorbance at 450 nm in an ELISA plate reader (ELx800 BIO-TEK Instruments Inc.).

Mixed Lymphocyte Reaction (MLR).

In the mixed lymphocyte reaction, stimulator cells cause responder cells to proliferate, owing to alloreactivity [Reich-Zeliger et al., 2004]. Splenocytes from 2c mice were stimulated by irradiated splenocytes from BALB/c mice in the presence of the evaluated compound at the concentrations specified. Cultures were incubated for 72 hours in 96-well plates.

Methylene Blue Assay.

The inhibitor-treated cultures and controls were fixed in glutaraldehyde, 0.05% final concentration, for 10 min at room temperature. After washing, the plates were stained with 0.1% methylene blue in 0.1 M borate buffer, for 60 min at room temperature. The plates were rigorously washed to remove excess dye and dried. The dye taken up by cells was eluted in 0.1N HCl for 60 min at 37° C., and the OD of the solution was read at 620 nm. In preliminary titration experiments, linear readings were obtained for $1×10^3$ to $4×10^4$ cells/well.

IL-2 Secretion.

Jurkat or PBMC cells were treated for 12 h with 1 µM, 0.5 µM or no inhibitor. Cells ($1×10^6$) were plated in 24-well plates (Nunc) and stimulated by C305 (dilution 1:500), anti-CD28 (1:100), PMA (50 ng/ml) or ionomycin (1 µM) for 12 h. Alternately, cells were stimulated for 24, 48 and 72 h in MLR. After stimulation cells were centrifuged at 130×g for 5 minutes at room temperature.

Supernatants were collected and IL-2 was assayed using the IL-2 ELISA kit (BioSource International USA, KH0022) according to the manufacturer's instructions. Absorbance was read at 450 nm in an ELISA plate reader (ELx800 BIO-TEK Instruments Inc.).

Cell Cycle Analysis.

The effects of the inhibition of the cell cycle were analyzed with a fluorescence-activated cell sorter (FACS). Cells were grown in 60 mm diameter plates (Nunc) and were treated with inhibitor for 12 and 24 h. After the indicated time, cells were pooled, pelleted by centrifugation, washed in phosphate-buffered saline (PBS), and fixed with cold 70% ethanol for a minimum of 12 h. Cells were re-pelleted and resuspended in PBS. 50 µg/ml of RNase A was added in the dark for 30 minutes followed by 5 µg/ml of propidium iodide for FACS analysis (Becton Dickinson FACScan).

Cell Stimulation and Lysis.

Jurkat cells were washed in PBS containing $Ca^{2+}$ and $Mg^{2+}$ (Biological Industries, Beit Haemek), preheated to 37° C. for 15 min, and were either mock stimulated with PBS, or were stimulated for 1 minute with C305 (1:500). Cells were then collected and lysed at a concentration of 2×10⁷ cells/ml in cold lysis buffer containing 1% NP-40, 10 mM Tris (pH 7.8), 150 mM NaCl, 1 mM phenylmethylsulfonyl fluoride (PMSF), 2 µg/ml pepstatin A, 1 µg/ml leupeptin, 10 mM sodium pyrophosphate, 0.4 mM EDTA, 0.4 mM sodium orthovanadate, and 50 mM NaF, 50 mM beta-glycerol phosphate pH 7.5 and 20 mM sodium pyrophosphate pH 7.5. After 20 min at 4° C., the lysates were cleared by centrifugation in a microfuge (Eppendorf, centrifuge 5427R) at 16,000×g for 10 min at 4° C. The supernatants were used directly for immunoprecipitation.

Western Blot.

Western blots were prepared on nitrocellulose using standard techniques. Membranes were blocked in TBST buffer (10 mM Tris-HCl, pH 7.4 (TBS), 0.2% Tween 20, 170 mM NaCl) containing 5% low-fat milk, then probed overnight with the appropriate primary antibody. After incubation with horseradish peroxidase-conjugated secondary antibody, immunoreactive proteins were visualized using an enhanced chemiluminescence (ECL) detection reagent.

Immunoprecipitation.

Bead preparation: 500 µl lysis buffer were mixed with 30 µL protein A (Roche, Germany) and the desired antibody, stirred at room temperature for 1 h, spun down and dried by vacuum. Cell lysates were obtained as described above and incubated with the beads for 1.5 h at 4° C. in a tumbling apparatus. The cells were centrifuged and washed 3 times with lysis buffer (the same lysis buffer used for cell lysis). Sample buffer was added and the samples were boiled for 3 min at 100° C. The supernatants were subjected to SDS-PAGE electrophoresis and western blotting.

SLP-76 Kinase Assay.

ZAP-70 was immunoprecipitated as described above. The immune complexes were washed 2 times with lysis buffer and 2 times with kinase buffer (50 mM Tris pH 7.5, 100 mM NaCl and 10 mM MgCl₂). The beads were resuspended in 30 µl of kinase buffer containing 3 µg of His-tagged, full-length human SLP-76 protein (kindly provided by Dr. Yablonski, Technion, Israel), and the kinase reactions were initiated by the addition of 10 µl kinase buffer containing 5 µM ATP. The reactions proceeded for 15 min at 30° C. and were stopped by the addition of 6 µL EDTA (100 mM) and sample buffer. The results were analyzed by western blot [Yablonski, 1998]

Example 1

Chemical Synthesis

Since protein kinases play crucial roles in signaling processes and cellular communication, we hypothesized that we might be able to find T cell proliferation inhibitors among compounds possessing chemical scaffolds used to generate protein kinase inhibitors. We therefore designed compounds based on the quinazoline moiety, an element that is present in many tyrosine phosphorylation inhibitors and a few serine/threonine kinase inhibitors. In our search for new specific inhibitors of T cell proliferation, we generated two libraries of quinazoline-based compounds.

The first library included the 2-(3,4,5-trimethoxyphenyl) quinazolin-4-amine derivatives of the general formula Ia, identified herein as compounds 1-19 (Table 2). The trimethoxyphenyl moiety was tested since it is a common pharmacophore for a variety of inhibitors, including inhibitors of tubulin polymerization [Sirisoma et al., 2009]; dihydrofolate reductase inhibitor [Baker et al., 1981], tyrosine and phosphoinositide kinases [Apsel et al., 2008]; and an HSP-90 inhibitor [Wright et al., 2004]. The second library included compounds having a 3,4,5-trihydroxyphenyl quinazoline skeleton, introduced to reduce hydrophobicity. The specific compounds prepared are the 5-(4-aminoquinazolin-2-yl)benzene-1,2,3-triol derivatives of the general formula Ib, identified herein as compounds 20-38 (Table 2). Compounds 1-19 were obtained by a multistep synthesis, starting from the chlorination of 2,4-quinolinedione by P(O)Cl₃ to give 2,4-dichloroquinazoline, followed by the addition of the corresponding aromatic amines. The reaction products were coupled with 3,4,5-trimethoxyphenylboronic acid catalyzed by Pd (II). Compounds 20-38 were prepared by the demethylation of compounds 1-19.

TABLE 2

Compounds 1-38

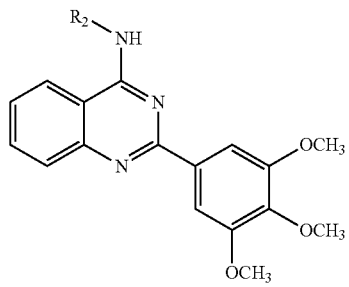

| Compound* | R₂ |
|---|---|
| 1 | phenyl |
| 2 | 4-methylphenyl |
| 3 | 2,4-dimethylphenyl |
| 4 | 4-hydroxyphenyl |
| 5 | 4-methoxyphenyl |
| 6 | 4-octyloxyphenyl |
| 7 | 4-trifluoromethoxyphenyl |
| 8 | 4-chlorophenyl |
| 9 | 2-hydroxymethylphenyl |
| 10 | benzyl |
| 11 | 4-aminobenzyl |
| 12 | 3,4-difluorobenzyl |
| 13 | 3,4-dichlorobenzyl |
| 14 | 4-methoxybenzyl |
| 15 | 1H-indazol-6-yl |
| 16 | 1H-indazol-5-yl |
| 17 | 2-(1H-indol-3-yl)-ethyl |
| 18 | benzo[1,3]dioxol-5-yl |
| 19 | 3H-benzoimidazol-5-yl |

Example 2

Compounds 1-38 Inhibit T Cell Proliferation

Since we were not prejudiced towards any specific protein kinase, we used a biological assay for T cell proliferation. We tested our libraries for inhibition of proliferation of PBMC and Jurkat cells (Table 3). Cell proliferation was measured by BrdU uptake. Jurkat cells do not need to be stimulated to proliferate. PBMC cells were stimulated by a non-specific T cell mitogen, Concanavalin A (ConA). All of the compounds that were tested inhibited proliferation at micromolar or submicromolar concentrations. Compound 2 possessed the highest inhibition potency, with an IC₅₀ of 70 nM for the inhibition of PBMC proliferation and 30 nM for the inhibition of Jurkat cell proliferation.

In view of the inhibition activities measured for each one of the compounds 1-38, the role of the aromatic amine ring on the activity of each one of the compounds, compared with that of compound 2 possessing the highest inhibition potency, was evaluated. As shown, elimination of the methyl group (compound 1) caused a 3-fold increase in the $IC_{50}$ of PBMC proliferation and a 10-fold increase in the $IC_{50}$ of Jurkat cell proliferation. The addition of another methyl at position 2 (compound 3) reduced the potency of the compound 10-fold in both cell lines. A bulky $OCF_3$ group (compound 7) increased the $IC_{50}$ by 5-fold for PBMC and 6-fold for Jurkat. OH or Cl groups at position 4 were similar in their potencies (compounds 4, 8). To assess the affect of flexibility and bond expansion, we replaced the aromatic amine ring with a benzyl amine (compounds 1, 10 and 5, 14). This substitution increased the $IC_{50}$ approximately 5-fold. 4-aminobenzyl was found to be more active than benzyl alone (compounds 11, 10). Dichloro and difluoro benzyls were similar in their abilities to inhibit proliferation (compounds 12, 13). Replacing the ring with indazole, indole, benzodioxol or imidazole (compounds 16, 17, 18, and 19, respectively) failed to improve activity. The trihydroxy compounds were less active than their trimethoxy analogs, with the exception of compound 31, showing inhibition activity that was similar to that of the trimethoxy analog 12.

TABLE 3

PBMC and Jurkat cells proliferation inhibition by compounds 1-38

| Compound | $IC_{50}$ (nM ± SD) | |
|---|---|---|
| | PBMC | Jurkat cells |
| 1 | 280 ± 0.04 | 380 ± 0.18 |
| 2 | 70 ± 0.05 | 29 ± 0.23 |
| 3 | 750 ± 0.05 | 2600 ± 3.39 |
| 4 | 300 ± 0.14 | 230 ± 0.04 |
| 5 | 500 ± 0.14 | 1100 ± 0.14 |
| 6 | 2400 ± 2.26 | 850 ± 0.07 |
| 7 | 400 ± 0.00 | 180 ± 0.11 |
| 8 | 300 ± 0.05 | 530 ± 0.32 |
| 9 | 850 ± 0.07 | 580 ± 0.18 |
| 10 | 3250 ± 2.47 | 600 ± 0.14 |
| 11 | 380 ± 0.04 | 480 ± 0.18 |
| 12 | 200 ± 0.00 | 730 ± 0.39 |
| 13 | 300 ± 0.14 | 730 ± 0.39 |
| 14 | 500 ± 0.14 | 1100 ± 0.14 |
| 15 | 450 ± 0.07 | 600 ± 0.14 |
| 16 | 600 ± 0.28 | 700 ± 0.35 |
| 17 | 750 ± 0.21 | 700 ± 0.35 |
| 18 | 380 ± 0.04 | 600 ± 0.00 |
| 19 | 430 ± 0.11 | 1500 ± 0.71 |
| 20 | 650 ± 0.49 | 5500 ± 3.50 |
| 21 | 850 ± 0.21 | 850 ± 0.21 |
| 22 | 730 ± 0.04 | 3700 ± 4.67 |
| 23 | 970 ± 0.84 | 1120 ± 0.28 |
| 24 | 500 ± 0.14 | 550 ± 0.21 |
| 25 | 4530 ± 0.31 | 4250 ± 1.30 |
| 26 | 2780 ± 0.26 | 3240 ± 0.31 |
| 27 | 550 ± 0.21 | 4250 ± 5.30 |
| 28 | 900 ± 0.14 | 650 ± 0.21 |
| 29 | 7000 ± 3.50 | 950 ± 0.07 |
| 30 | 570 ± 0.24 | 670 ± 0.22 |
| 31 | 280 ± 0.04 | 600 ± 0.21 |
| 32 | 2600 ± 0.24 | 3640 ± 0.54 |
| 33 | 3260 ± 0.49 | 5430 ± 0.76 |
| 34 | 500 ± 0.14 | 690 ± 0.30 |
| 35 | 780 ± 0.67 | 710 ± 0.87 |
| 36 | 1240 ± 0.74 | 1970 ± 0.74 |
| 37 | 5500 ± 6.36 | 800 ± 0.28 |
| 38 | 4340 ± 0.74 | 2570 ± 0.82 |

Example 3

S101 Specifically Inhibits the CD3+ Cell Population

Figure 1B:
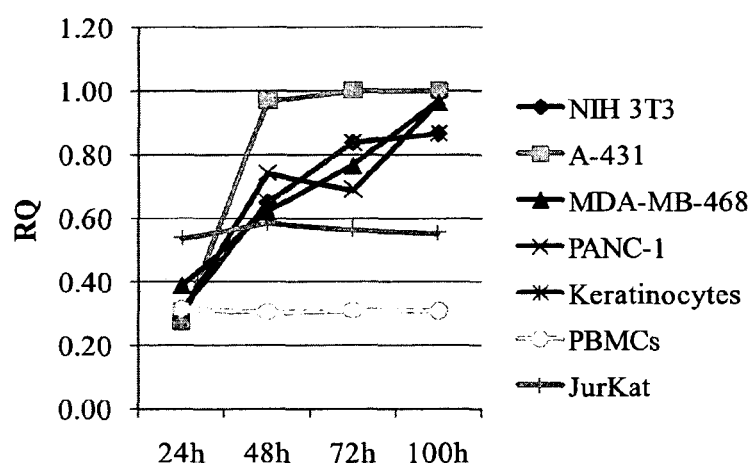
Figure 2A:
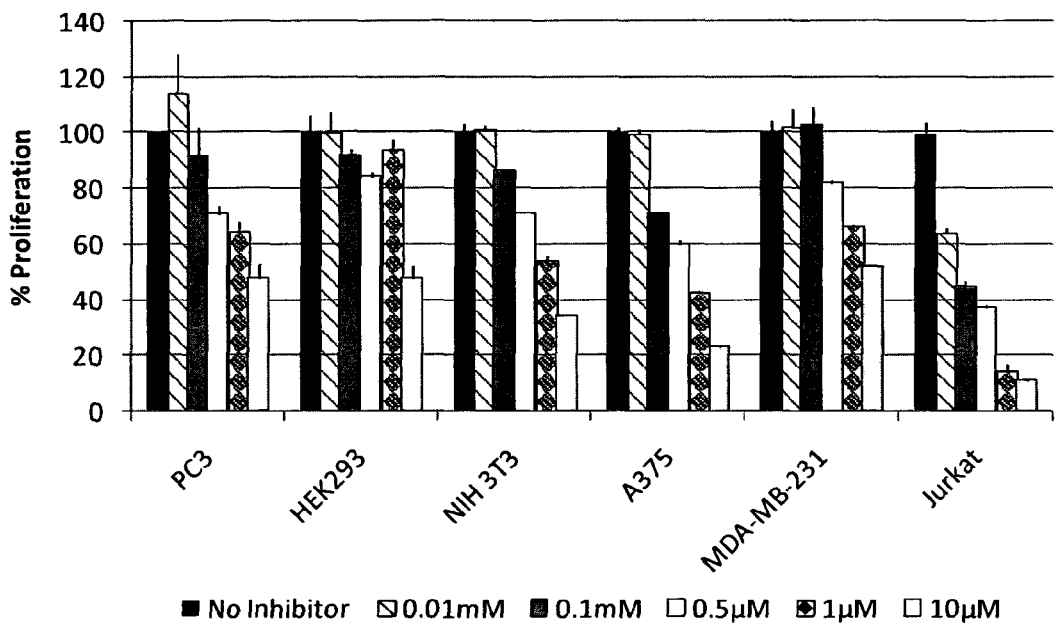
FIGS. 2A-C depicts the effect of compound 2 (S101) on the growth of various cell lines. A. BrdU uptake of the cells without stimulation B. BrdU uptake of the stimulated cells: ConA (10 µg/ml) activated PBMC, serum activated HEK293 and A375, PDGF (30 ng/ml) activated NIH 3T3, EGF (30 ng/ml) activated MDA-MB-231 were treated with increasing inhibitor concentrations. C. Growth curves of the selected cells without inhibitor and after treatment with 1 µM inhibitor, relevant quantification (RQ) to growth without inhibitor's treatment. IC$_{50}$ values of the non-stimulated and stimulated cells are shown in Table 4.
Figure 2B:
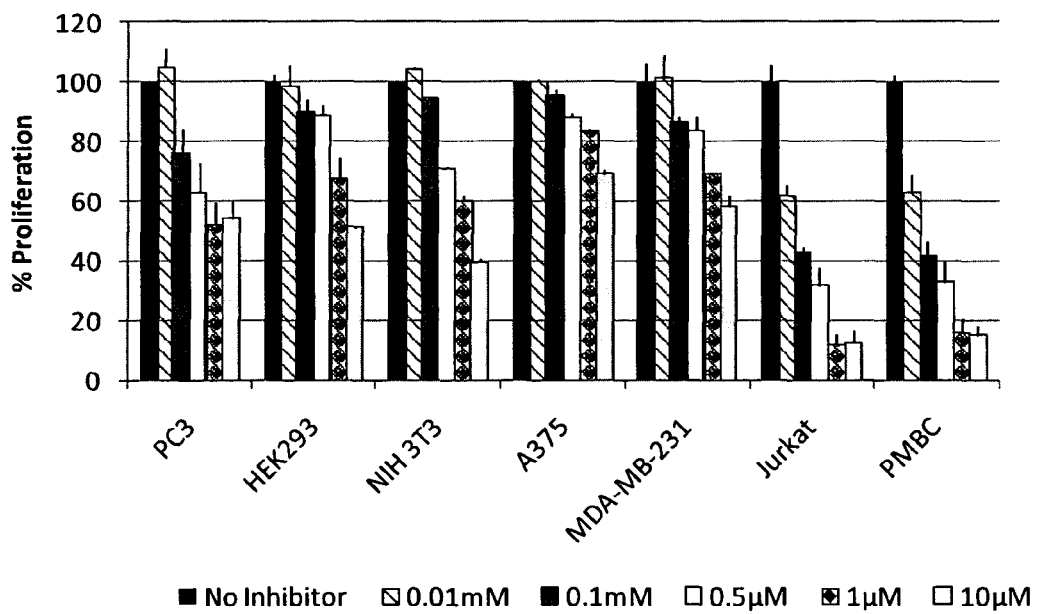
Figure 2C:
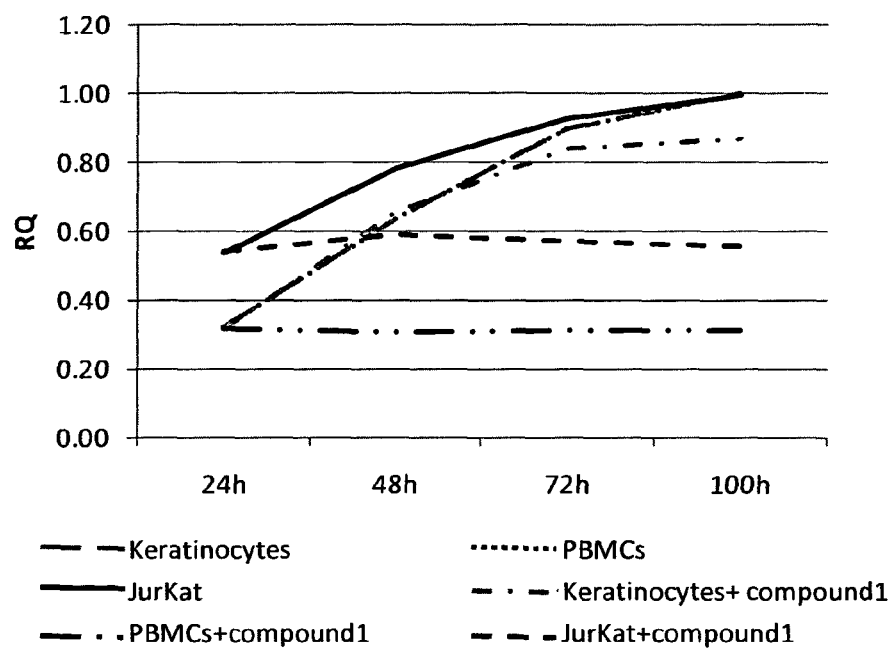

To characterize the mode of action of 2 (S101) in more detail, we first examined whether 2 inhibits non-hematopoietic cell lines. We studied the effect of 2 on the growth of four cell lines: NIH 3T3 (mouse embryonic fibroblasts), A-431 (human vulval carcinoma cells), MDA-MB-468 (human breast carcinoma cells), and PANC-1 (human pancreatic carcinoma cells) (FIGS. 1A-B). We also tested the inhibitors on human keratinocytes. The inhibitor slightly affected these cell types at high concentrations, at which the growth of Jurkat and PBMC was strongly inhibited (FIG. 2C). We also examined the effect of 2 on BrdU uptake by stimulated and non-stimulated PC-3 (human prostate cancer), HEK293 (human embryonic kidney), NIH-3T3, A375 (human malignant melanoma), and MDA-MB-231 (human breast adenocarcinoma). The effect of the inhibitor on the proliferation of the various cells had $IC_{50}$ values higher by two orders of magnitude in comparison to the inhibitory $IC_{50}$ for PBMC and Jurkat cells (Table 4).

TABLE 4

| Cell line | $IC_{50}$ of non-stimulated cells (µM) | $IC_{50}$ of stimulated cells (µM) |
|---|---|---|
| Jurkat | 0.05 | 0.1 |
| PBMC | 0.05 | — |
| Keratinocytes | — | >10 |
| PC3 | ~10 | >10 |
| HEK293 | ~10 | ~10 |
| A375 | ~0.8 | >10 |
| NIH3T3 | ~3 | ~7 |
| MDA-MB-231 | >10 | >10 |

Figure 3A:
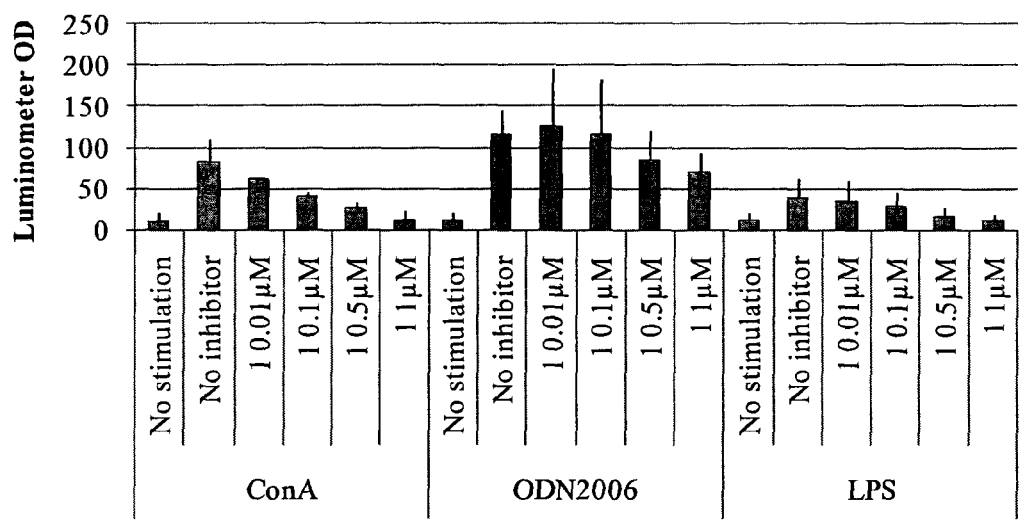
FIGS. 3A-C show activation and inhibition of PBMC, CD3+ cells and PBMC depleted of CD3+ cells. PBMC were stimulated with (10 µg/ml) ConA, (0.5 µg/ml) ODN2006 (Enzo Life Sciences), or (50 µg/ml) LPS (A), CD3+ cells were stimulated with ConA (B), and PBMC depleted of CD3+ cells were stimulated with both ODN2006 and LPS, in the presence and absence of inhibitor (C). Their proliferation was measured by uptake of BrdU and normalized to the maximal proliferation in the absence of inhibitor.
Figure 3B:
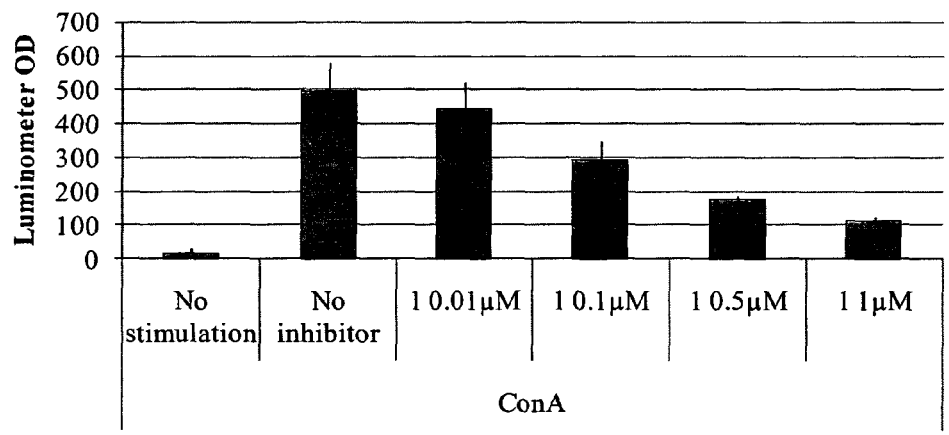
Figure 3C:
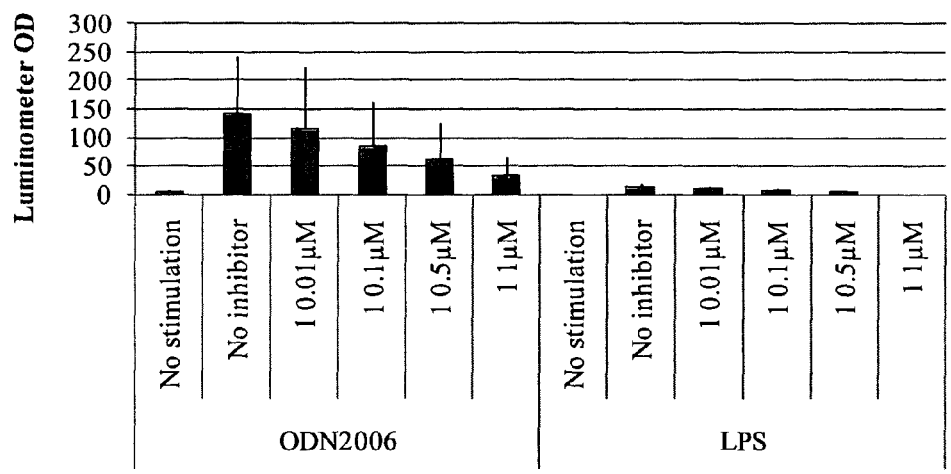

PBMC consist of a mixture of mononucleated cells, mostly T cells. To identify the cell type that was inhibited by 2, we first purified T cells from PBMC with an autoMACS apparatus (Miltenyi Biotec), using anti-CD3 antibodies. We were now able to compare three cell populations: total PBMC, CD3+ cells purified from PBMC, and PBMC that had been depleted of CD3+ cells. In order to test the effect of 2 on the various cell populations, we made use of three modes of stimulation: (1) ConA, which stimulates T cells exclusively; (2) ODN2006 (Oligodeoxynucleotide 5'-tcgtcgttttgtcgttttgtcgtt-3'), which stimulates mainly non-T cells, via Toll-like Receptor-9 (TLR9), which is highly expressed on dendritic cells, B lymphocytes and natural killer (NK) cells; and (3) lipopolysaccharide (LPS), which stimulates mostly B cells, macrophages and some T cells. To test the inhibition by 2 of PBMC proliferation, we used all three stimuli, namely ConA, ODN2006, and LPS. ConA-stimulated proliferation was strongly inhibited by 2, with an $IC_{50}$ of ~0.1 µM. ODN2006 and LPS-stimulated proliferation of PBMCs was inhibited to a lesser extent, with an $IC_{50}$ of ~0.5 µM (FIG. 3D), which was similar to the $IC_{50}$ of 2 for PBMCs that had been depleted of CD3+ cells, whether stimulated by ODN2006 or LPS (FIG. 3F). The proliferation of isolated CD3+ cells was very strongly inhibited by 2, with an $IC_{50}$ that was slightly higher than 0.1 µM (FIG. 3E). These data show that 2 specifically inhibits the proliferation of CD3+ T cells, and has a much lesser effect on the non-T cell fraction of the PBMC. These results suggest that 2 affects cell growth factors that are unique to CD3+ T cells.

Example 4

S101 Specifically Arrests T Cells in G2

Figure 4A:
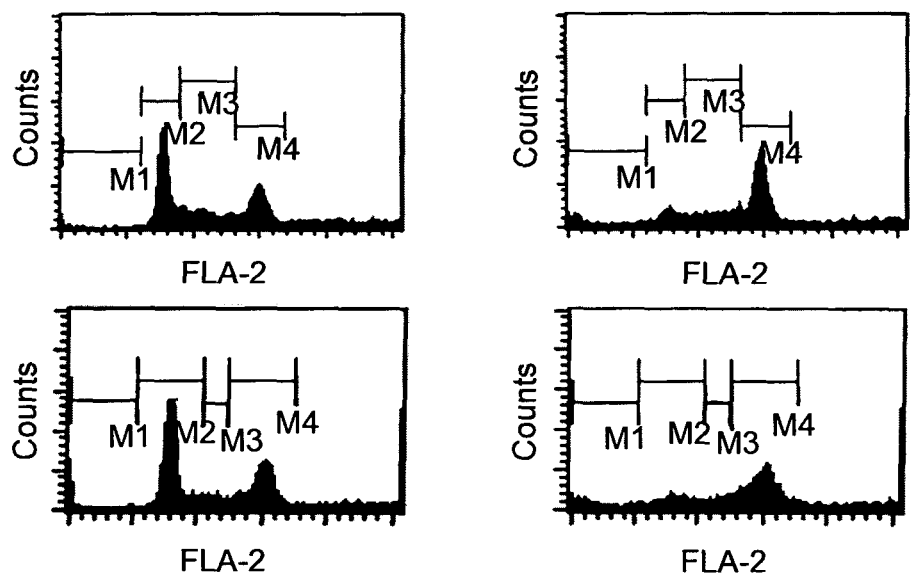
FIGS. 4A-B show the effect of compound 2 (S101) on the cell cycle of PBMC and Jurkat cells. A. Cellular G2 arrest and apoptosis as a result of S101 treatment. Distribution in subG1 (represented by M1), G1 (M2), S (M3), or G2/M (M4) phase was determined by FACS analysis. Jurkat (1 and 2): 1 without inhibitor, and 2 in the presence of 0.5 µM S101. PBMC (3 and 4): 3 without inhibitor, and 4 in the presence of 0.5 µM S101. The x-axis shows DNA content; and the y-axis shows the number of cells. B. Graphic quantification of the cell cycle.
Figure 4B:
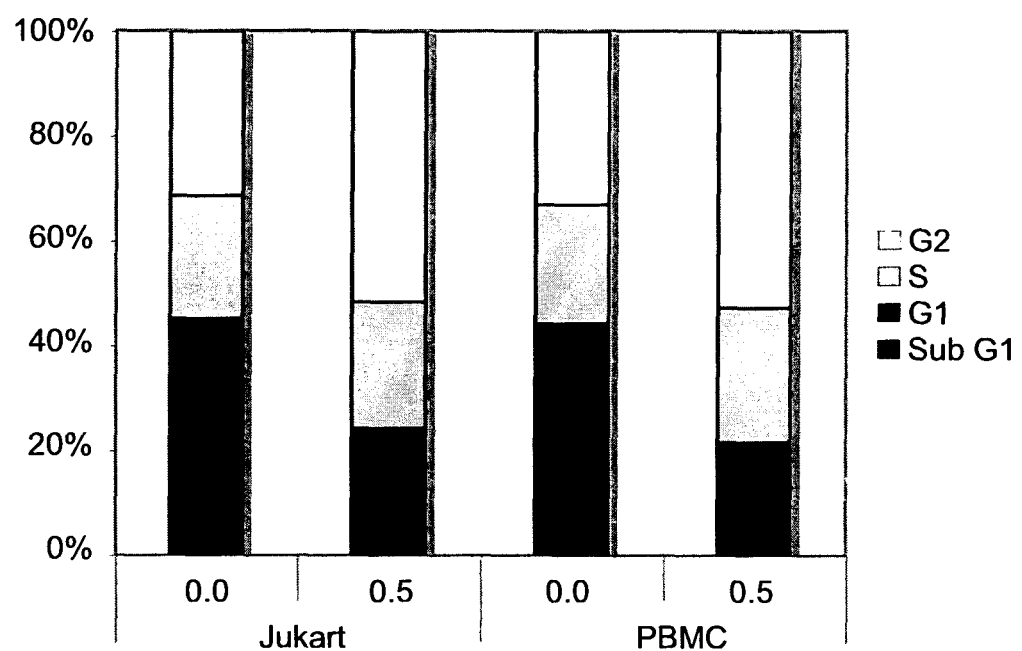

FACS analysis revealed that treatment of PBMC and Jurkat cells with 2 led to arrest at the G2 phase of the cell cycle. The fraction of cells in G2 increased from 30% in the untreated cells to 50% in the treated cells. The sub-G1 population increased from 2% to 9.5%, indicating that some cells underwent apoptosis (FIG. 4).

Example 5

S101 Inhibits T Cell Proliferation without Affecting IL-2 Secretion

Figure 5A:
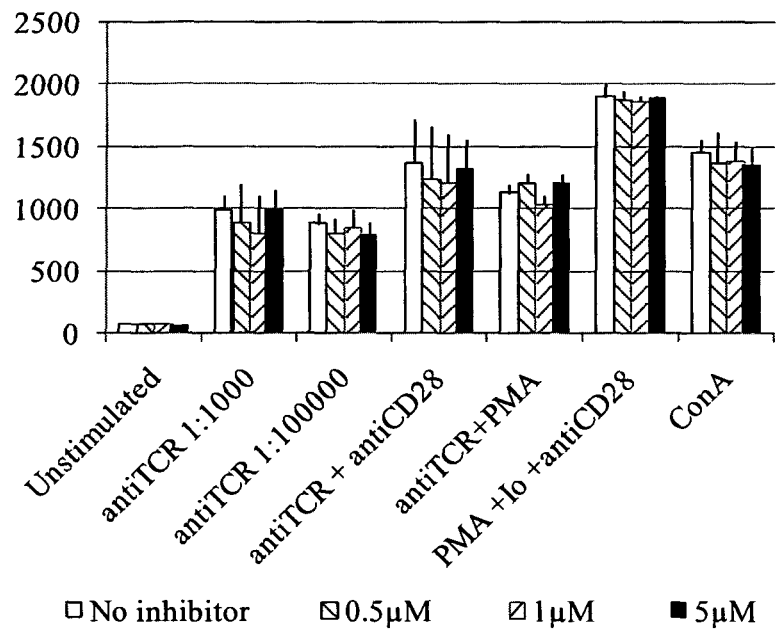
FIGS. 5A-C depict IL-2 secretion after stimulation. IL-2 levels in the growth medium were measured by ELISA after centrifuging out the cells. A. Jurkat cells. B. PBMC. Four modes of stimulation were used in order to examine the inhibitor's ability to affect diverse events in the T cell. First, cells were stimulated using anti-TCR antibody, attached to the plate. The coupling of the antibody to TCR initiates a signal transduction cascade, leading to cell proliferation and secretion of IL-2. Second, anti-TCR antibody was used in combination with an antibody to the CD28 molecule. This combination of signaling via the TCR as well as the co-stimulatory effect induced higher levels of IL-2. Third, ionomycin (a calcium ionophore; Io), phorbol 12-myristate 13-acetate (PMA; a PKC activator) and the antibody for CD28, were used in combination. This stimulation activated parallel pathways and gave rise to the highest IL-2 level. Fourth, ConA stimulation served as control to proliferation assays. The experiment was executed with both Jurkat and PBMC. Compound 2 (S101) did not affect IL-2 secretion in either cell type, irrespective of the mode of stimulation. PBMC had lower IL-2 levels. C. MLR; Splenocytes from 2C mice were stimulated by irradiated splenocytes from BALB/c mice in the presence of compound 2, compound 21 (S145, negative control) or Cyclosporine A (CsA; positive control) at the concentrations specified. Cultures were incubated for 72 hours in 96-well plates. Supernatants were collected after 24, 48 and 72 h and IL-2 was assayed.
Figure 5B:
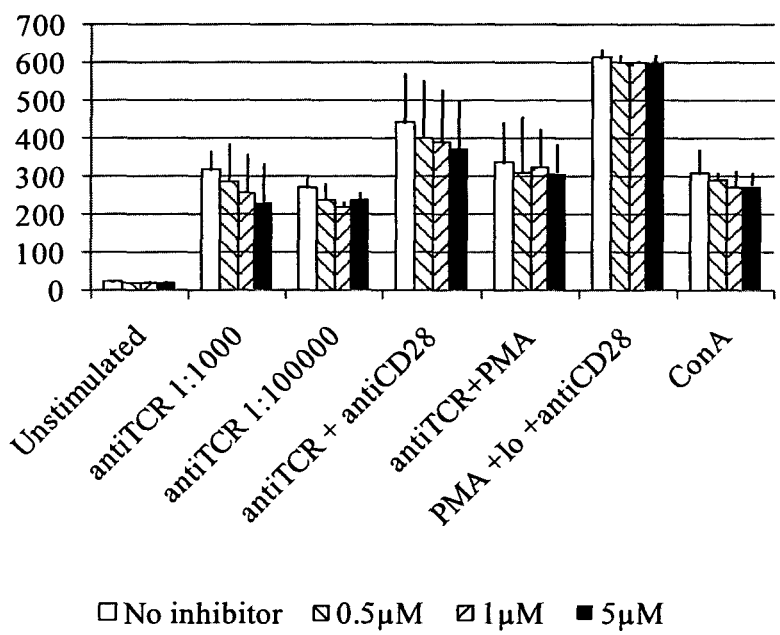

As mentioned above, IL-2 is secreted in an autocrine manner by T cells to induce their own proliferation Jurkat cells, which originate from leukemia, divide with no need of exogenous IL-2 stimulation since they produce their own, whereas PBMC proliferation requires exogenous IL-2 for growth. As expected, IL-2 secretion levels were lower in cells isolated from the blood (PBMC) than in Jurkat cells (FIGS. 5A-B). We analyzed the effect of 2 on IL-2 secretion in both Jurkat (FIG. 5A) and PBMC (FIG. 5B) cells, using a variety of T cell stimuli. Cells were stimulated with an antibody to the TCR alone or in combination with anti-CD28 or phorbol 12-myristate 13-acetate (PMA). In order to bypass the TCR, we also stimulated the cells with a combination of ionomycin, PMA and anti-CD28 (FIG. 5A). We were surprised to discover that the inhibitor did not act by repressing IL-2 secretion. Irrespective of the mode of stimulation, compound 2 had no effect on IL-2 levels in the medium, up to a concentration of 5 µM inhibitor.

Figure 5C:
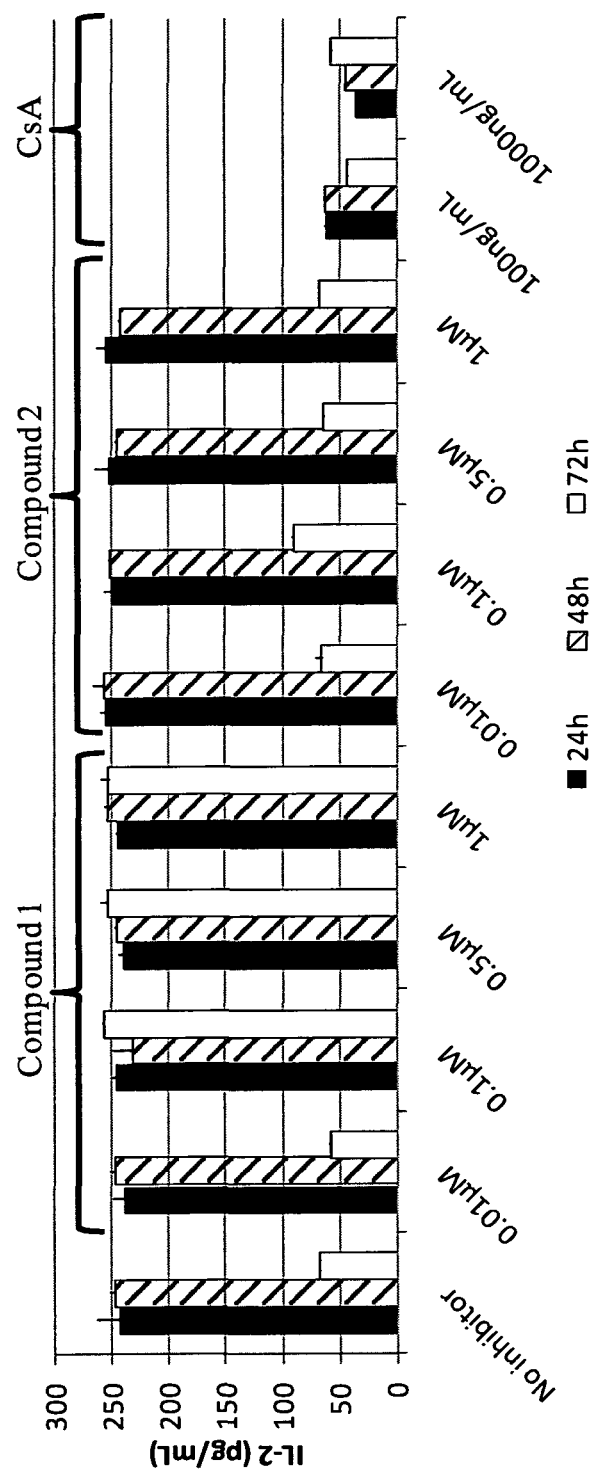

In vivo, T cells are stimulated by neighboring cells. In order to test the effect of 2 on cell-stimulated IL-2 secretion, the supernatants of splenocytes after 24, 48 and 72 h MLR were collected and analyzed for their IL-2 levels (FIG. 5C). Without inhibitor, or in the presence of S145 (compound 21) levels of IL-2 decreased after 72 h, probably due to the consumption of IL-2 by proliferating cells. This effect was not seen with compound 2, because the cells did not proliferate. Treatment with cyclosporine A, which is known to repress IL-2 transcription, led to a marked decrease in IL-2 levels in the medium, as early as 24 h after initiation of treatment. In the presence of 2, no visible decrease in IL-2 secretion was detectable even at 1 µM inhibitor (FIG. 5C). At higher concentrations, no viable cells remained. These findings lead us to conclude that the dramatic inhibition by 2 of proliferation is caused by a distinct, novel mechanism that does not involve IL-2 secretion.

Example 6

S101 Inhibits Tyrosine Phosphorylation of SLP-76

We were intrigued by the properties of 2 and its analogs, especially by the finding that IL-2 secretion was not inhibited, in contrast to known T cell anti-proliferative agents, and by the effect of 2 on the cell cycle. We therefore began to search for cellular targets of 2.

The T cell receptor and co-receptor are associated with the Src-family protein kinases, Fyn and Lck. It is thought that binding of a peptide:MHC ligand to the T cell receptor and co-receptor brings together CD4, the T-cell receptor complex, and CD45 [Jackman et al., 1995]. This allows the CD45 tyrosine phosphatase to remove inhibitory phosphate groups on Fyn and Lck. Phosphorylation of the ζ chains on the receptor enables them to bind and activate the cytosolic tyrosine kinase ZAP-70 [Pedro E. Paz, 2001]. ZAP-70 phosphorylates the adaptor protein SLP-76 (Src homology 2 (SH2) domain-containing leukocyte protein of 76 kDa), which in turn leads to the activation of PLC-γ by Tec kinases and the activation of Ras by guanine-nucleotide exchange factors. Thus, SLP-76 is one of the key elements in T cell signaling following T cell receptor activation.

Figure 6A:
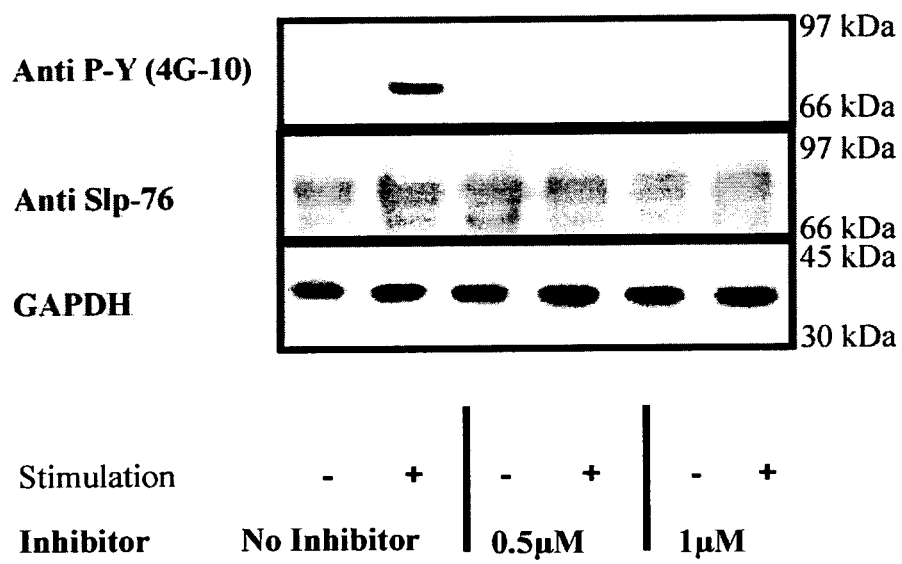
FIGS. 6A-B show that compound 2 inhibits phosphorylation on SLP-76. A. Jurkat cells were treated with inhibitor and SLP-76 was immunoprecipitated from the cell lysate. Phosphorylated SLP-76 was visualized by western blot using 4G-10 (top) and anti-SLP-76 (middle), GAPDH served as loading control. B. Jurkat cells were treated with inhibitor, lysed and ZAP-70 immunoprecipitated. Recombinant SLP-76 was added and a kinase assay performed. Phosphorylated SLP-76 was visualized by western blot, using the antiPY antibody 4G-10.
Figure 6B:
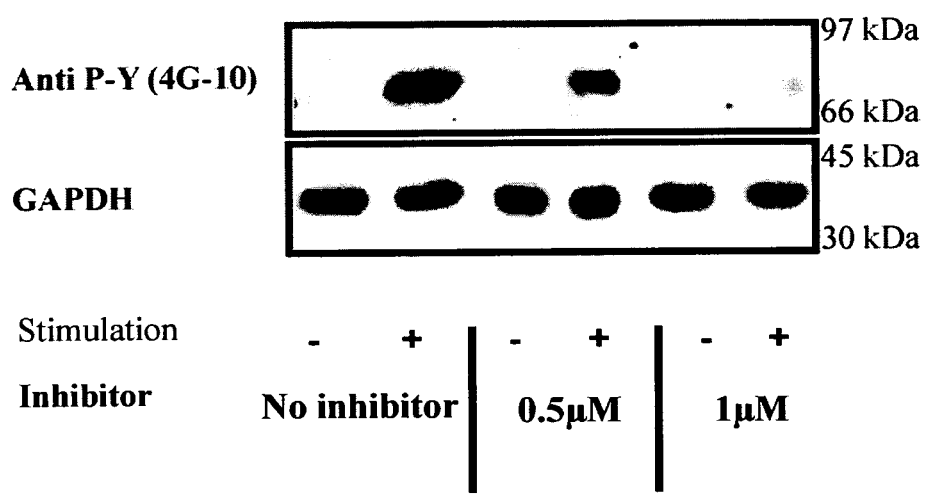

Jurkat cells were treated with 2 for 16 h, and SLP-76 phosphorylation was measured by immunoprecipitation of SLP-76 protein followed by western blotting with an antibody to the phosphorylated tyrosines of the protein (FIG. 6A). We also immunoprecipitated the ZAP-70 kinase from the treated/untreated cells, and tested its ability to phosphorylate recombinant SLP-76 protein as substrate (FIG. 6B). 2 inhibited the activity of ZAP-70, as well as tyrosine phosphorylation of SLP-76, in a dose-dependent manner, indicating that 2 acts upstream of SLP-76. Although in SLP-76 deficient Jurkat cells, no IL-2 is produced [Yablonski et al., 1998] at the concentrations we tested (up to 1 µM), SLP-76 phosphorylation was reduced but not abolished. Presumably the remaining SLP-76 activity was sufficient to allow IL-2 secretion.

Example 7

S101 Inhibits Both CD4+ and CD8+ Populations

Mice used included male and female 6- to 12-week-old CB6/F1 mice, obtained from the Roscoe B. Jackson Memorial Laboratory (The Jackson Laboratory, Bar Harbor, Me., http://www.jax.org). A breeding pair of transgenic (Tg) H-2b mice expressing the T-cell antigen receptor (TCR) 1B2 from the CD8+ clone 2C with specificity for H-2Ld was kindly provided by Janko Nikolic-Zugic (Memorial Sloan-Kettering Cancer Center, New York, http://www.mskcc.org). A breeding pair of Tg H-2b mice expressing the TCR from the CD4+ clone known as TEA with specificity for I-Ead allopeptide, cross-presented by host APC and bound to I-Ab and was kindly provided by Alexander Y. Rudensky (University of Washington, Seattle). I-Ead allopeptide corresponds to the positions 52 to 68 from the alpha-chain of I-E class II molecules and is expressed in all APCs from H-2b/I-E+ strains (CB6F1-hybrid of C57BL/6 and Balb/c). C57BL/6 mice are H-2b but I-E−, whereas BALB/c are H-2d and I-E+, and therefore their F1 hybrids are H-2b/1-E+ and able to directly present antigen.

Mixed Lymphocyte Reaction (MLR).

Responder 2C splenocytes were harvested, and the cell suspensions were treated with Tris-buffered ammonium chloride to remove RBC. The isolated cells (2×106/ml) were stimulated with irradiated (20 Gy) BALB/c, splenocytes (2×106/ml), which express H-2d. Responders (2×106/ml) and stimulators (2×106/ml) were cultured for 3 days in RPMI 1640 complete tissue culture medium at 37° C. in a 5% $CO_2$/air incubator. On day 3, the MLR cultures were harvested, and analyzed by FACS for CD4 or CD8 levels.

Cytofluorometric Analysis.

FACS analysis was performed using a modified FACScan (BD Biosciences, Mountain View, Calif.). Fluorescence data were collected during one minute.

Annexin V-Cy5 was used to detect apoptotic cells. Cells were incubated in annexin V binding buffer and supplemented with 5 µl of annexin V-Cy5. The cells were incubated at room temperature for 5 min in the dark, then washed in binding buffer. Positive cells were monitored by flow cytometry.

The ability to monitor the fate of 2C and TEA responder cells by FACS enabled us in the present study to verify the role of 2 in the proliferation inhibition by measuring the levels of double-positive CD8+1B2+ or double-positive CD4+/Va2+ cells in the presence or the absence of the inhibitor. In the case of the former, only animals with high expression are chosen. As shown in FIGS. 7A-D the percentage of these double-positive effector cells in a typical experiment was reduced in a dose dependent manner within 72 h after incubation, whereas no reduction was observed when compared to a different inhibitor (compound 21, S145 or vehicle (DMSO).

Figure 7A:
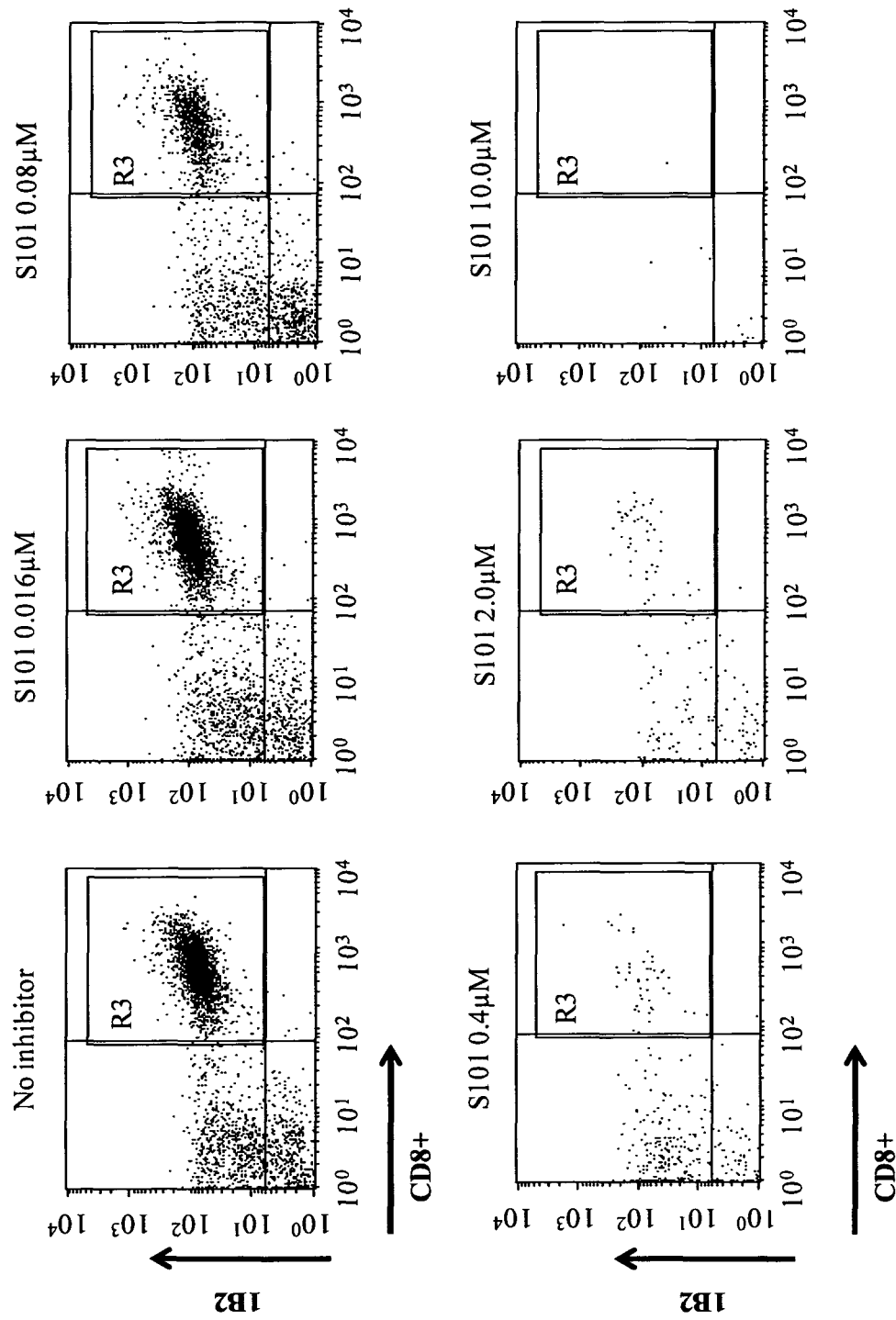
Figure 7B:
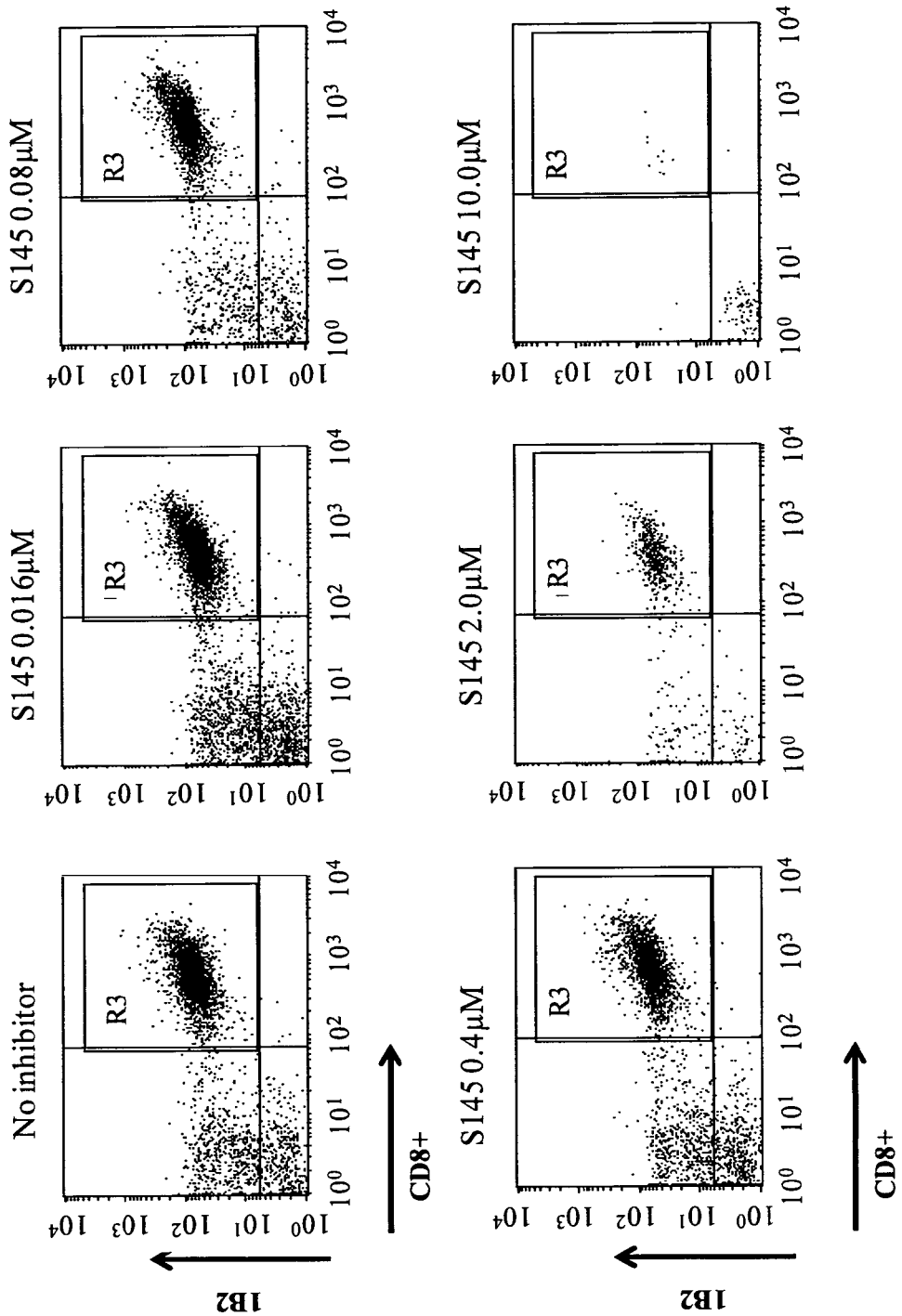
Figure 7E:
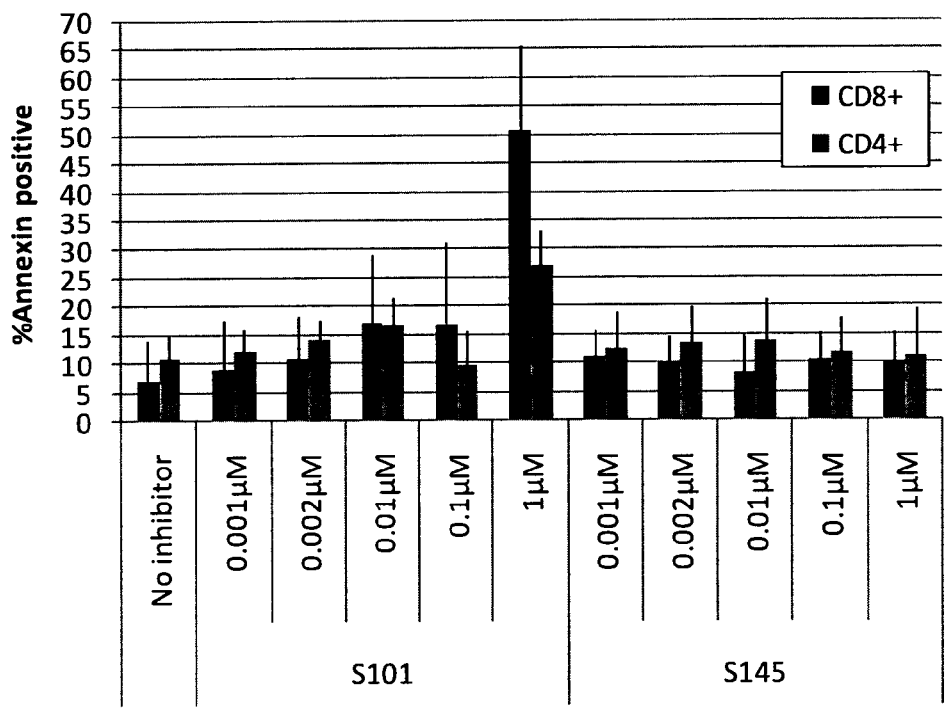

Furthermore, triple staining with annexin V, FIG. 7E showed that this pattern of deletion coincided with the induction of annexin V on the effector cells, i.e. with the induction of apoptotic cell death.

Figure 7F:
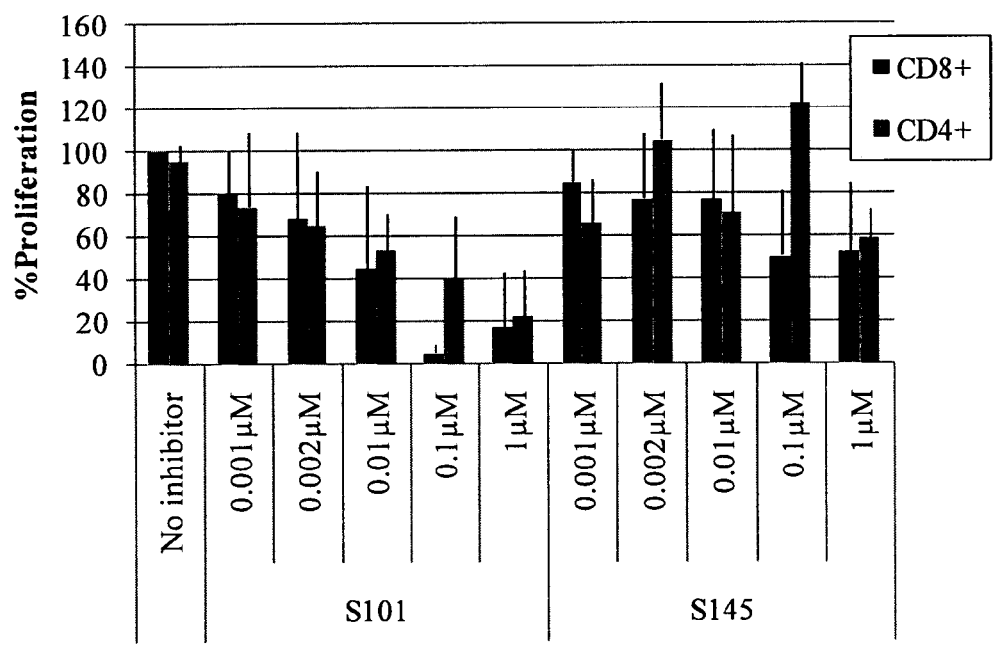

The inhibitor showed similar inhibition potency for both types of T cells, with a slight preference to CD8+ cells (FIG. 7F).

Example 8

S101 Inhibits Proliferating but not Non-Proliferating CD4+ and CD8+ T Cells

The aim of this test was to determine whether 2 affects only the proliferating cells or there is a general mechanism affecting all cell numbers. For this purpose we mixed 3 cell types: for CD4+: BALB/c, 2C and OT1; for CD8+: CB6F1, TEA and OT2. The OT1 and OT2 are splenocytes that were isolated from OT1 and OT2 mice (Jackson Laboratories, Bar Harbor, Me.), The cells were chosen for control cells that do not proliferate, because they are not induced to proliferate in this experimental set-up and there is a straightforward method to detect them using FACS. Thus, the ability to monitor the fate of proliferation and resting cells by FACS was enabled due to the use of the MLR described above for CD4+ and CD8+ and the addition of OT2 and OT1 splenocytes, respectively.

Proliferating cells often secrete cytokines that induce survival of neighbouring cells; since the proliferation was expected to be inhibited we added 50 ng/ml of IL-7. This concentration is sufficient to keep the cells alive, but not to induce proliferation.

Irradiated Balb splenocytes were incubated for 72 h with 2C, and OT1 splenocytes in the presence of IL-7 W/O inhibitor.

Figure 8A:
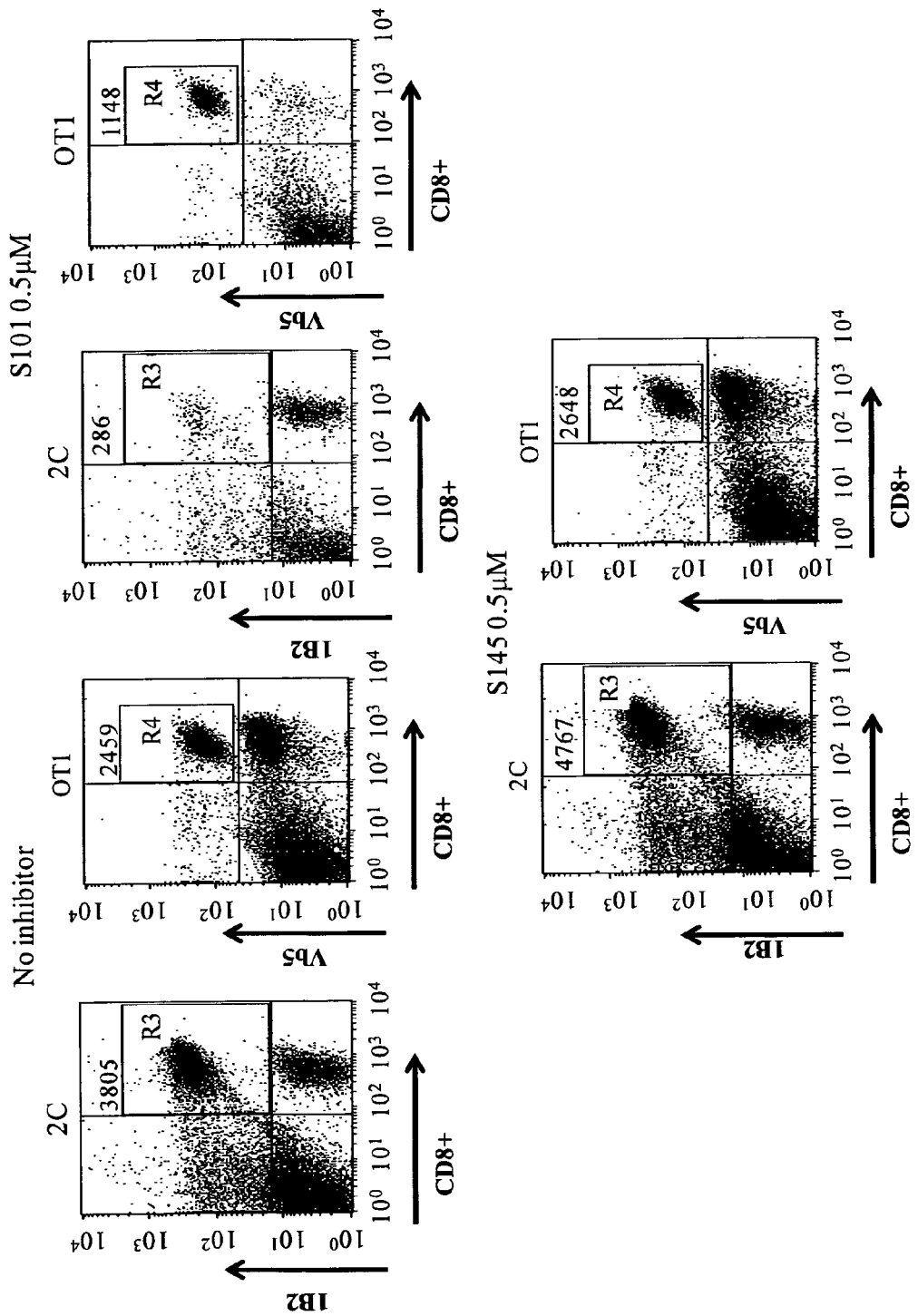
FIGS. 8A-D show the effect of compound 2 (S101) on proliferating and non-proliferating and CD8+ T cells. OT1 were incubated in the CD8+ (2C cells) MLR cultures with or without IL-7 in the presence or absence of the inhibitor. A. FACS dot plot comparison of cell numbers after 72 h MLR. B. FACS histogram plot of the Anexin V positive cells. C and D. Cell numbers and Annexin V positive cells, respectively.

The CD4+ and CD8+ were stimulated to proliferate, whereas in the absence of specific stimuli the OT1 and OT2 cell populations were resting, and theses cells were kept alive by the administration of IL-7. As shown in FIG. 8A, the number of 2C (stimulated) and OT1 (resting) cells that were not treated with an inhibitor was 3805 and 2459, respectively. The number of 2C and OT1 cells that were treated with 0.5 µM 2 was 286 and 1148, respectively, while the number of 2C and OT1 cells that were treated with 0.5 µM 21 (control) was 4767 and 2468, respectively. This is depicted as a bar-graph in FIG. 8C.

FIG. 9A shows that the number of TEA (stimulated) and OT2 (resting) cells that were not treated with an inhibitor was 3850 and 1025, respectively. The number of TEA and OT2 cells that were treated with 0.5 µM 2 was 1452 and 826, respectively, while the number of 2C and OT1 cells that were treated with 0.5 µM 21 was 3003 and 903, respectively. This is depicted as a bar-graph in FIG. 9C.

In all, FIGS. 7 and 8 show that the number of the resting cells remained the same in the presence of 2 whereas the number of the stimulated cells was reduced.

Figure 8B:
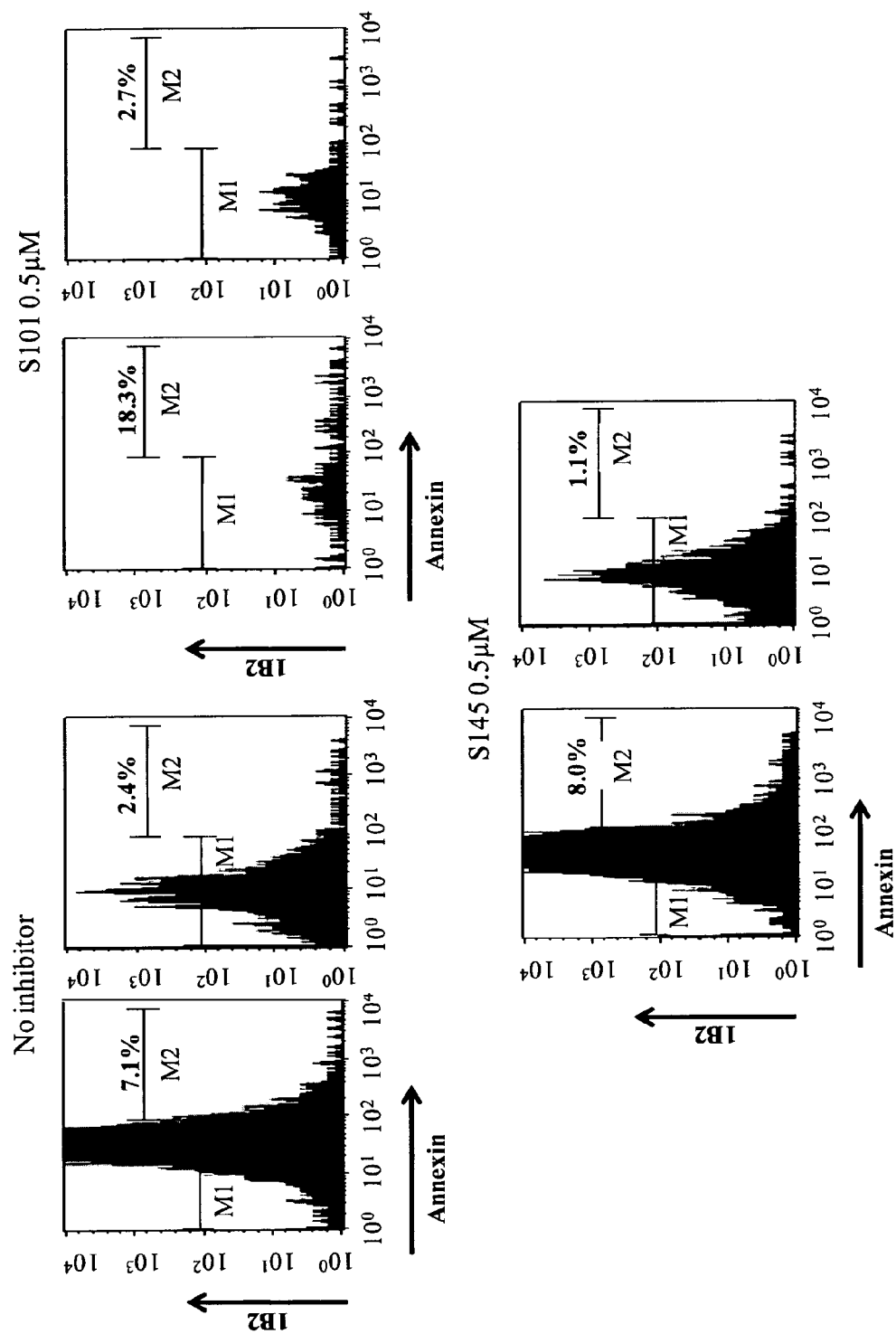
Figure 8C:
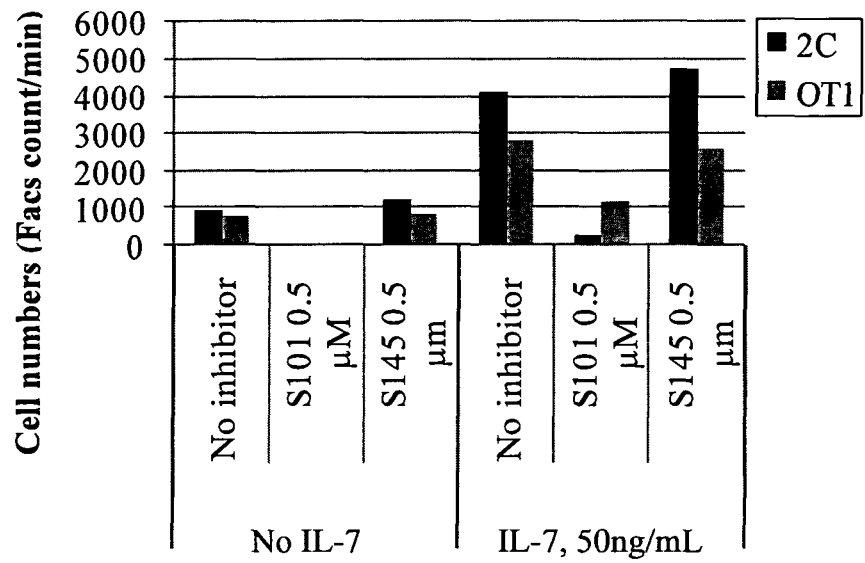
Figure 8D:
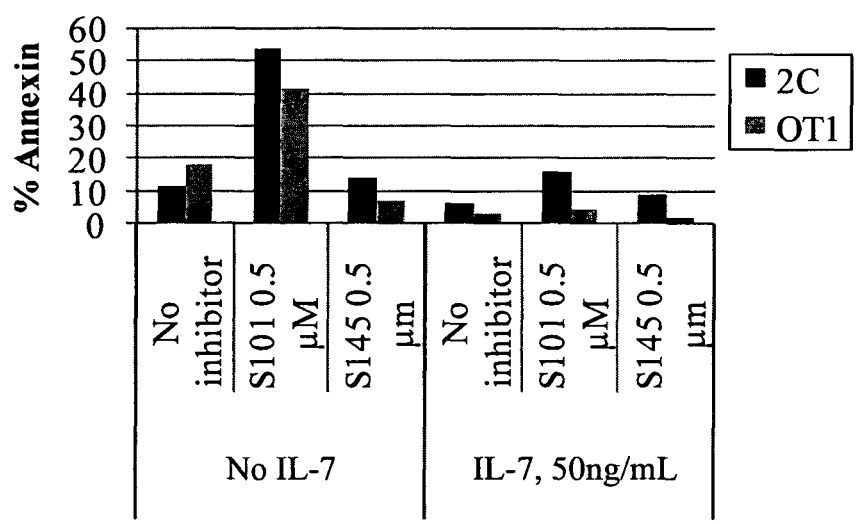
Figure 9B:
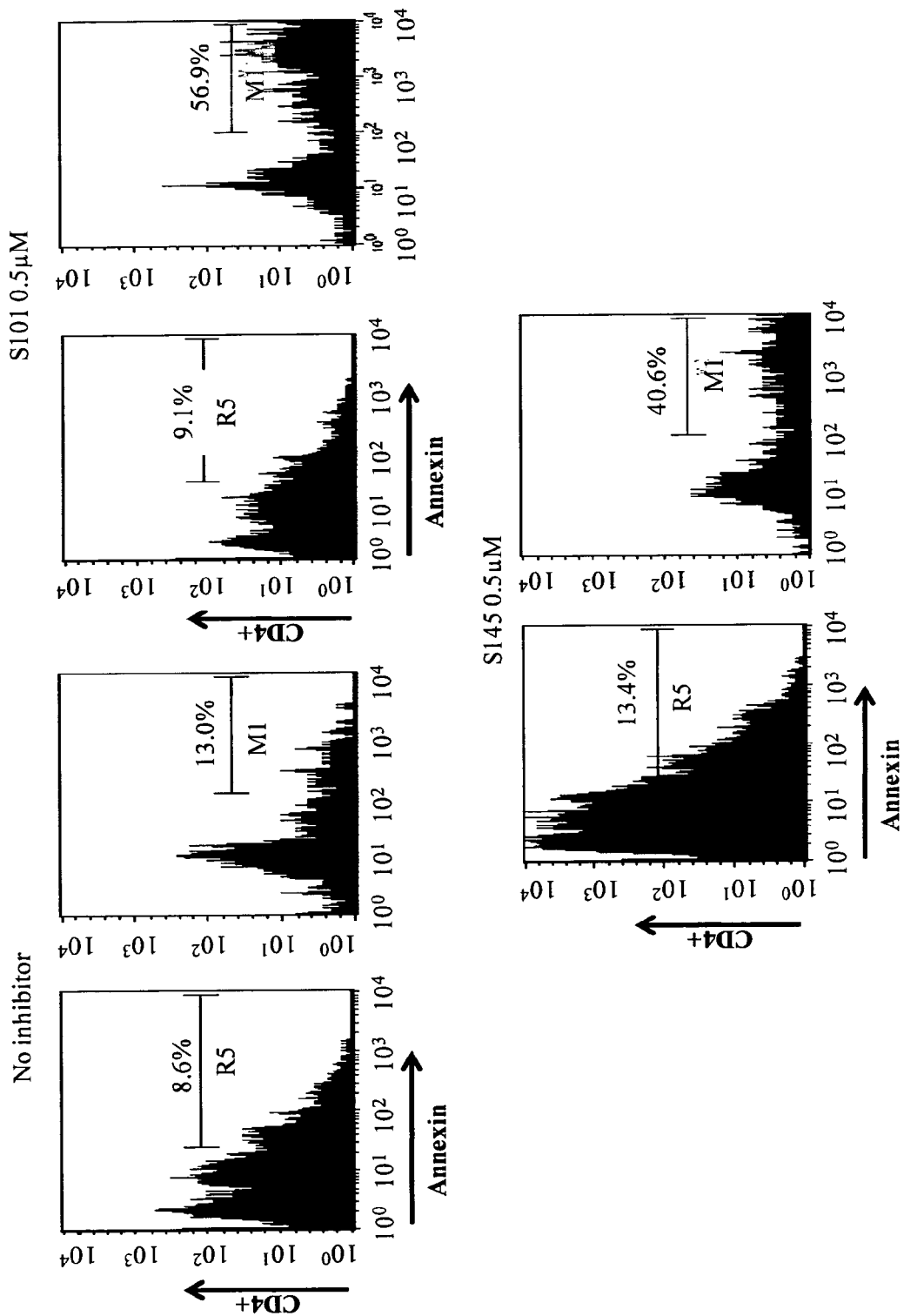
Figure 9C:
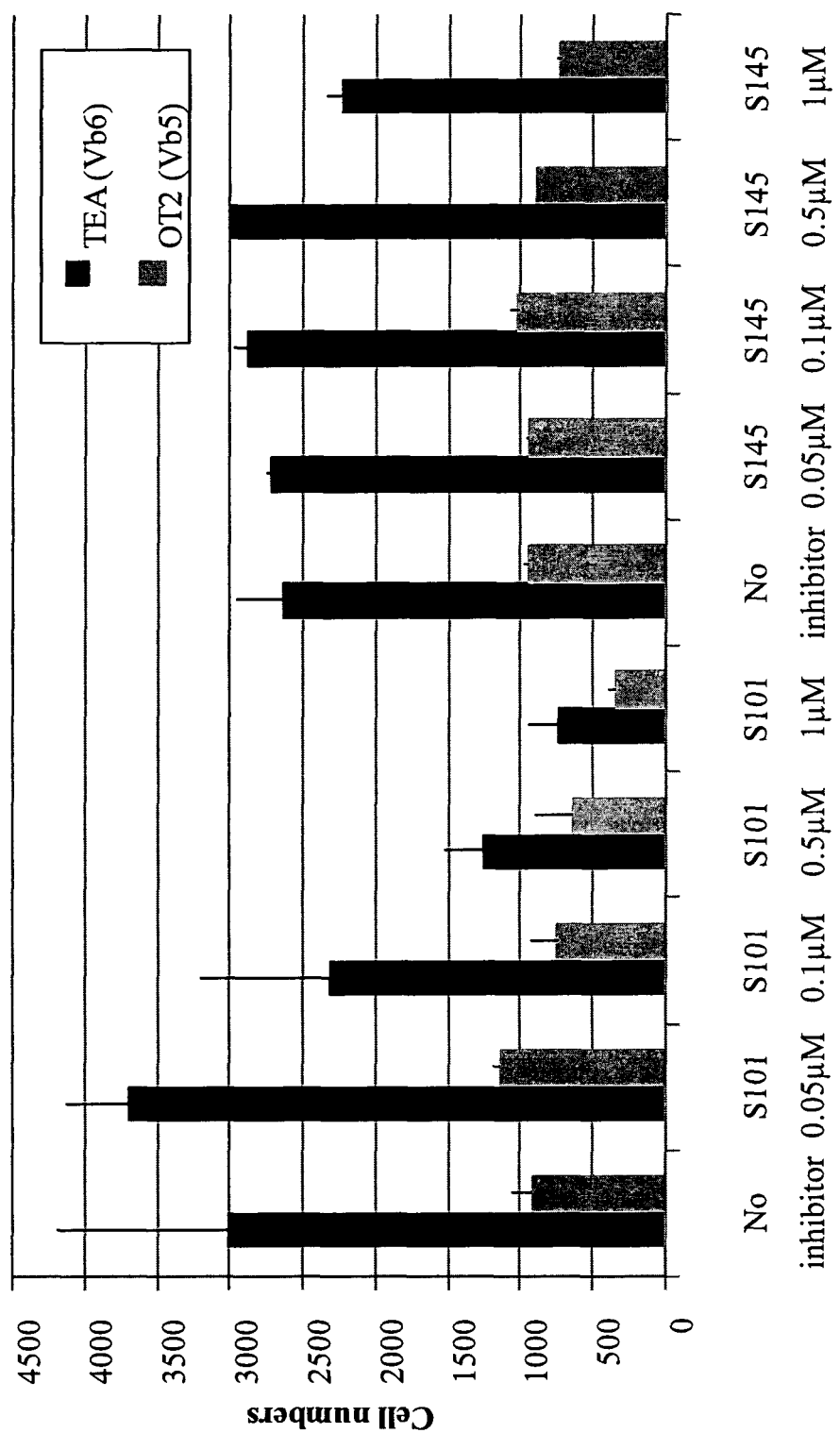
Figure 9D:
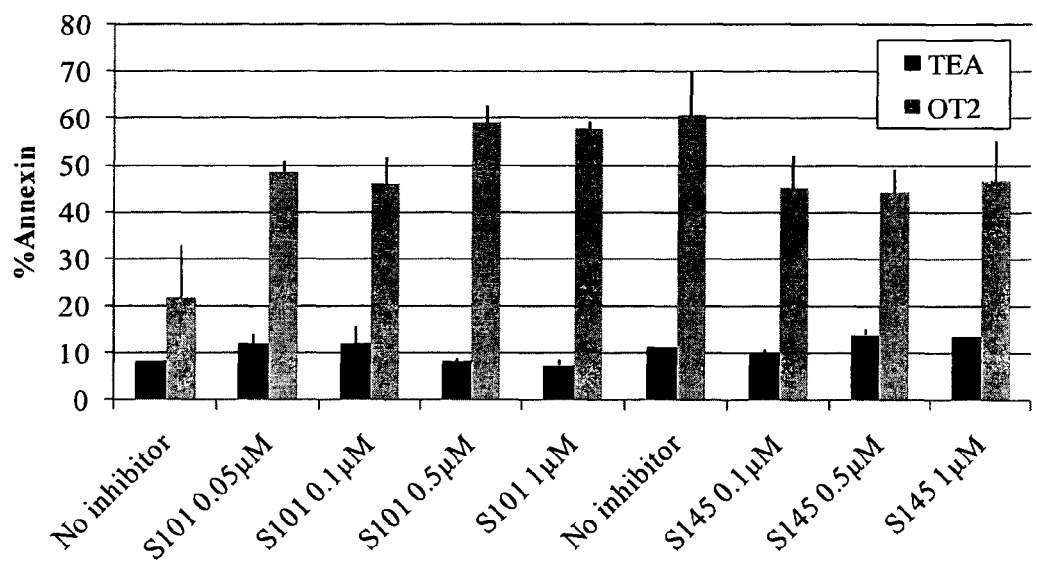

The fraction of 2C or OT1 cells and TEA and OT2 cells displaying annexin V on the cell surface is shown in FIG. 8B and FIG. 9B, respectively. Bar graphs summarizing these findings are shown in FIG. 8D and FIG. 9D, respectively. In accordance to the MLR results the triple staining with annexin V, FIG. 8D and FIG. 9D show that this pattern of deletion coincided with the induction of annexin V on the effector cells, i.e. the number of stimulated cells decreased at least in part due to apoptotic cell death.

Example 9

S101 Inhibits Graft Rejection

Animals.

Six- to 12-week-old female mice were used throughout the experiments. Balb/c-Nude mice were obtained from the Weizmann Institute Animal Breeding Center (Rehovot, Israel). C3H/HeJ mice were obtained from the Roscoe B. Jackson Memorial Laboratory (Bar Harbor, Me., USA). All mice were kept in small cages (five animals in each cage) and fed sterile food and acid water containing 20 µg/ml cyprofloxacin (Bayer AG, Leverkusen, Germany).

T Cell-Mediated Allograft Rejection Model.

C3H/HeJ female mice were exposed to a single dose of 10 Gy (lethal dose) TBI on day 0. The following day, the mice received intravenously $1.5 \times 10^4$ purified host T cells (HTCs). Transplantation of $3 \times 10^6$ allogeneic Balb/c-Nude BM cells was performed on day 2 in conjunction with the tolerizing compound to be evaluated. The survival of the mice was monitored daily.

Host T-Cell Preparation.

Splenocytes of host C3H/HeJ mice were fractionated on Ficoll/Paque, and the isolated mononuclear cells were subjected to a positive selection of T cells (CD4 plus CD8) by magnetic cell sorting (MACS, Miltenyi Biotec, Bergisch Gladbach, Germany). Cytofluorimetric analysis of the fractionated cells was carried out by triple immunofluorescent staining using the following directly labeled antibodies (Pharmingen, San Diego, Calif., USA): fluorescein isothiocyanate-CD4/L3T4 (clone H129.19), phycoerythrin (PE)-CD3e (clone 145-2C11), and Cy-Chrome-CD8a/Ly-2 (clone 53-6.7).

Example 10

T Cell-Mediated BM Allograft Rejection and GVHD Model

Splenocytes of the donor mice are cultured against irradiated host splenocytes for 72 h in the presence of the inhibitor. Subsequently, CD8 cells are positively selected using Magnetic Particles (BD Pharmingen). The isolated cells are host nonreactive CD8 cells. Since the cells were mixed with host splenocytes, the reactive sub-set of cells reacted by proliferation and were eliminated, the rest of the population which did not show the autoreactive feature survived, i.e. they are host nonreactive.

Host C3H mice are supralethally irradiated (10 Gy) on day-2, and on day 0 receive a transplant of $5 \times 10^6$ allogeneic NUDE BM cells with or without the isolated cells evaluated for GVHD activity (cells treated with the inhibitor). The mice are monitored for survival and weight loss.

Example 11

Percutaneous Absorption and Penetration Studies of S101

Animals.

Fresh porcine ears were obtained from local slaughterhouse. Dorsal side skin was surgically removed from the ears. Hairs were trimmed off with an electric trimmer. Subcutaneous fat was carefully cleaned. The skin samples had an average thickness of about 700 µm. They were stored at −20° C. until use.

Formulations.

Compound 2 was dispersed into Labrasol® (Gattefosse, France) The mixture was heated to 35° C. and stirred until solubilized. Final concentrations: 0.108% and 0.316%. The final products are clear and somewhat viscous solutions.

In Vitro Percutaneous Absorption and Penetration Studies.

The skin samples were mounted on Zyleris' High-Throughput Screening (HTS) station. Each individual cell has a diffusion area of 0.503 cm$^2$ (8 mm in diameter). The receptor chamber was filled with 2.0 ml of 5% Oleth-20 in 1×PBS buffer, pH 7.4 (10 mM Phosphate, 138 mM NaCl and 2 mM KCl), which was continuously mixed at 200 r.p.m. The screening experiments were carried out at 32±0.1° C. Oleth-20 is a polyethylene glycol ether of Oleyl Alcohol [Poly(oxy-1,2-ethanediyl) 20 mol Ethylene Oxide average molar ratio] (Spectrum Chemical, California).

The samples were dosed at 5 mg for both formulations. Each formulation was run in three replicates. At the end of each time interval (2, 12, and 24 h), the skin surface was wiped with cotton ball. The standard tape-stripping method was used to remove the stratum corneum (SC) layer. Repeated tape-stripping was continued until SC layer was disappeared (15 strips). Compound 2 absorbed in epidermis/dermis layer was collected by solvent extraction with DMSO. After tape-stripping, the remaining skin samples were minced and vortexed with 1.5 ml DMSO. The supernatant was separated. The extraction step was repeated three times. The supernatants were combined and ready for analysis.

LC-MS/MS Analytical Methods.

The analysis was carried out with a Shimadzu LC-10ADVP instrument with Varian Polaris 3 C18-A, 50×3.0 mm, column. Mobile Phase A: 0.1% formic acid in water. Mobile Phase B: 0.1% formic acid in methanol. Flow rate: 0.4 ml/min.

MS system is an AB Scienx API4000 operated at positive ionization mode. The calibration range is 2.50-25,000 ng/ml.

Results

Quality Control Data.

Quality control of the screening experiments was established by measuring mass balances of a couple of selected runs (spot-check). Measurement of mass balance is to determine total amount of 2 recovered after each experiment. After the selected experiments, total amount of 2 left on the skin surface, absorbed in stratum corneum, in epidermis/dermis layer, and collected in the receptor medium was extracted and determined by LC-MS/MS analysis. The total amount was then compared to the initial dosing amount to determine recovery percentage. Two of the 12 hr runs for the 0.316% formulation was selected for the spot-check. The recovery percentages were found to be 89% and 114%, respectively. They are within acceptable range of 80-120%.

Penetration to the Epidermis/Dermis Layer.

Figure 10:
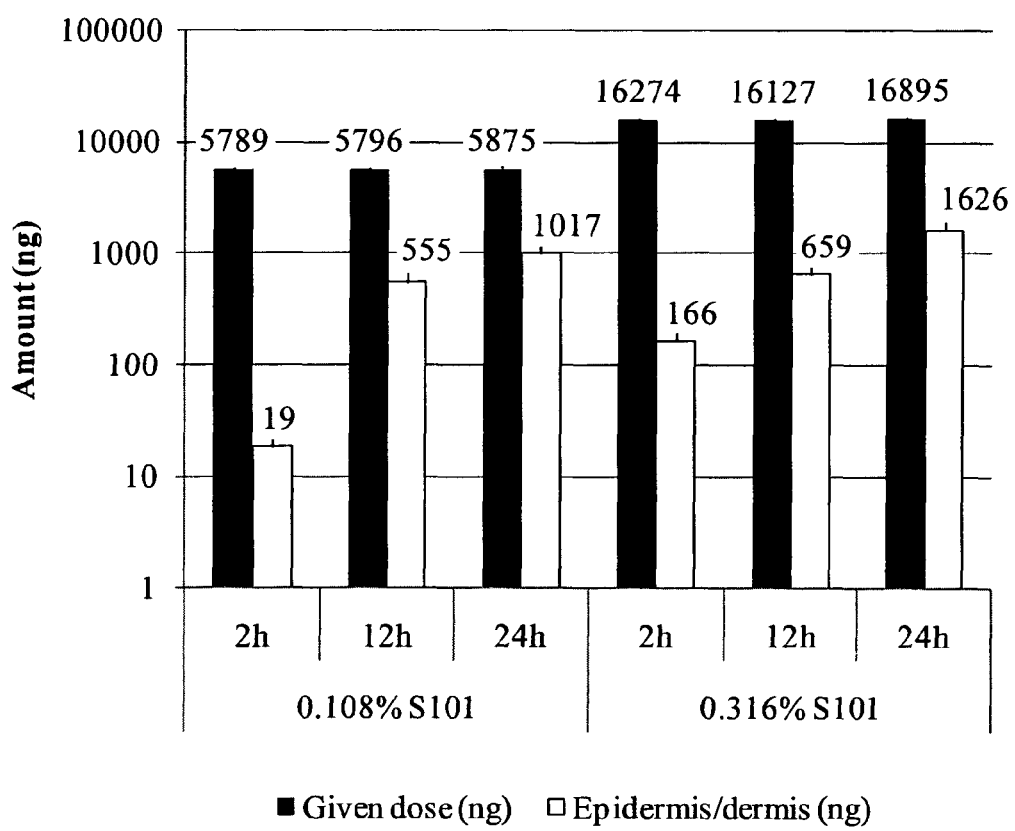
FIG. 10 shows that compound 2 (S101) has the ability to penetrate the skin. A comparison between the S101 given dose on skin surface and the amount extracted from the epidermis/dermis. Black bars, Given dose; White bars, Dose measured in epidermis/dermis.

Compound 2 was able to penetrate the epidermis/dermis layer of the porcine ears skin. As seen in FIG. 10, after 24 h at an initial concentration of 0.3% 2 in Labrasol, the final concentration in the skin is estimated to be higher than 114 µM (1000 folds higher than the $IC_{50}$).

REFERENCES

Abraham, R. T. and G. J. Wiederrecht (1996) "Immunopharmacology of rapamycin." *Annu Rev Immunol* 14: 483-510.

Aherne, G. W., E. Ward, et al. (1998). "Comparison of plasma and tissue levels of ZD1694 (Tomudex), a highly polyglutamatable quinazoline thymidylate synthase inhibitor, in preclinical models." *Br J Cancer* 77(2): 221-6.

Allison, A. C. (2000). "Immunosuppressive drugs: the first 50 years and a glance forward." *Immunopharmacology* 47(2-3): 63-83.

Allison, A. C., S. J. Almquist, et al. (1991). "In vitro immunosuppressive effects of mycophenolic acid and an ester pro-drug, RS-61443." *Transplant Proc* 23(2 Suppl 2): 10-4.

Apsel, B., J. A. Blair, et al. (2008). "Targeted polypharmacology: discovery of dual inhibitors of tyrosine and phosphoinositide kinases." *Nat Chem Biol* 4(11): 691-9.

Baker, D. J., C. R. Beddell, et al. (1981). "The binding of trimethoprim to bacterial dihydrofolate reductase." *FEBS Lett* 126(1): 49-52.

Brasca, M. G., N. Amboldi, et al. (2009). "Identification of N,1,4,4-tetramethyl-8-{[4-(4-methylpiperazin-1-yl)phenyl]amino}-4,5-dihydro-1H-pyrazolo[4,3-h]quinazoline-3-carboxamide (PHA-848125), a potent, orally available cyclin dependent kinase inhibitor." *J Med Chem* 52(16): 5152-63.

Chiu, L. M., B. M. Domagala, et al. (2004). "Management of opportunistic infections in solid-organ transplantation." *Prog Transplant* 14(2): 114-29.

Cohn, R. G., A. Mirkovich, et al. (1999). "Mycophenolic acid increases apoptosis, lysosomes and lipid droplets in human lymphoid and monocytic cell lines." *Transplantation* 68(3): 411-8.

Curtis, J. J., Luke, R. G., Duborsky, E. (1986). "Cyclosporine in therapeutic doses increases renal allograft vascular resistance." *Lancet* 2: 477-479.

Dayton, J. S., L. A. Turka, et al. (1992). "Comparison of the effects of mizoribine with those of azathioprine, 6-mercaptopurine, and mycophenolic acid on T lymphocyte proliferation and purine ribonucleotide metabolism." *Mol Pharmacol* 41(4): 671-6.

Dodge, I. L., Li, X. C., Strom, T. B (1999). "Rapamycin induces TGF-b production in lymphocytes." *Transplantation* 67.

Georgina H. Cornish, L. V. S., and Doreen A. (2006). "Cantrell Differential regulation of T-cell growth by IL-2 and IL-15." *Blood* (108): 600-608.

Gonzalez, J., T. Harris, et al. (2001). "Rapamycin blocks IL-2-driven T cell cycle progression while preserving T cell survival." *Blood Cells Mol Dis* 27(3): 572-85.

Haussmann, W. (2000). "Mechanisms of Action of Immunosuppressants and Immunoinductors." *Contrib Oncol* 55: 62-93.

Herman, W. H., Hircik, D. E., Simonson, M. S (1999). "Cyclosporine activates the endothelin converting enzyme: implications for acute and chronic nephrotoxicity." *Transplantation* 67.

Herrmann, M. L., R. Schleyerbach, et al. (2000). "Leflunomide: an immunomodulatory drug for the treatment of rheumatoid arthritis and other autoimmune diseases." *Immunopharmacology* 47(2-3): 273-89.

Hojo, M., T. Morimoto, et al. (1999). "Cyclosporine induces cancer progression by a cell-autonomous mechanism." *Nature* 397(6719): 530-4.

Itoh, H. A. H. (1993). Immunosuppressive drugs: developments in anti-rejection therapy. *Hodder Arnold*. A. Thomson, Oxford Uni Pr: 161-176.

Jackman, J. K., D. G. Motto, et al. (1995). "Molecular cloning of SLP-76, a 76-kDa tyrosine phosphoprotein associated with Grb2 in T cells." *J Biol Chem* 270(13): 7029-32.

Jones, T. R., A. H. Calvert, et al. (1981). "A potent antitumour quinazoline inhibitor of thymidylate synthetase: synthesis, biological properties and therapeutic results in mice." *Eur J Cancer* 17(1): 11-9.

Ka, S. M., A. Rifai, et al. (2006). "Glomerular crescent-related biomarkers in a murine model of chronic graft versus host disease." *Nephrol Dial Transplant* 21(2): 288-98.

Kino, T., H. Hatanaka, et al. (1987). "FK-506, a novel immunosuppressant isolated from a Streptomyces. II. Immunosuppressive effect of FK-506 in vitro." *J Antibiot* (Tokyo) 40(9): 1256-65.

Levitzki, A. and E. Mishani (2006). "Tyrphostins and other tyrosine kinase inhibitors." *Annu Rev Biochem* 75: 93-109.

Liu, J., J. D. Farmer, Jr., et al. (1991). "Calcineurin is a common target of cyclophilin-cyclosporin A and FKBP-FK506 complexes." *Cell* 66(4): 807-15.

Nagarathnam Dhanapalan, A. D., Shao Joanxing, Liu Xiao-Gao, Khire Uday, Wang Chungung, Hart Barry, Boyer Stephen (2002). Rho-kinase inhibitors. PCT/US02/08659.

Ong, C. K., P. Lirk, et al. (2007). "An evidence-based update on nonsteroidal anti-inflammatory drugs." *Clin Med Res* 5(1): 19-34.

Onur Boyman, H. P. H., Curdin Conrad, Brian J. Nickoloff, Mark Suter, and F. O. NestleSpontaneou (2004). "Spontaneous development of Psoriasis in a New Animal Model Shows an Essential Role for Resident T Cells and Tumor Necrosis Factor-α." *J. Exp. Med.* 199.

Pedro E. Paz, S. W., Holly Clarke, Xaiobin Lu, David Stokoe and Arie Abo (2001). "Mapping the Zap-70 phosphorylation sites on LAT (linker for activation of T cells) required for recruitment and activation of signaling proteins in T cells." *Biochem. J* (305): 461-471

Reich-Zeliger, S., J. Gan, et al. (2004). "Tolerance induction by veto CTLs in the TCR transgenic 2C mouse model. II. Deletion of effector cells by Fas-Fas ligand apoptosis." *J Immunol* 173(11): 6660-6.

Rollinghoff, M., A. Starzinski-Powitz, et al. (1977). "Cyclophosphamide-sensitive T lymphocytes suppress the in vivo generation of antigen-specific cytotoxic T lymphocytes." *J Exp Med* 145(2): 455-9.

Sirisoma, N., A. Pervin, et al. (2009). "Discovery of N-(4-methoxyphenyl)-N,2-dimethylquinazolin-4-amine, a potent apoptosis inducer and efficacious anticancer agent with high blood brain barrier penetration." *J Med Chem* 52(8): 2341-51.

Skelton, L. A., M. G. Ormerod, et al. (1998). "Cell cycle effects of CB30865, a lipophilic quinazoline-based analogue of the antifolate thymidylate synthase inhibitor ICI 198583 with an undefined mechanism of action." *Cytometry* 33(1): 56-66.

Theti, D. S., V. Bavetsias, et al. (2003). "Selective delivery of CB300638, a cyclopenta[g]quinazoline-based thymidylate synthase inhibitor into human tumor cell lines overexpressing the alpha-isoform of the folate receptor." *Cancer Res* 63(13): 3612-8.

Thomson, A. W. (1994). "Immunosuppressive drugs and the induction of transplantation tolerance." *Transpl Immunol* 2(4): 263-70.

Turk, J. L. (1964). "Studies on the Mechanism of Action of Methotrexate and Cyclophosphamide on Contact Sensitivity in the Guinea Pig." *Int Arch Allergy Appl Immunol* 24: 191-200.

Waer, M. (1996). "The use of leflunomide in transplantation immunology." *Transpl Immunol* 4(3): 181-5.

William R. Perrault, K. P. S., Lori A. LaPean, Mark A. Krook, Paul J. Dobrowolski, Mark A. Lyster, Moses W. McMillan, Donald J. Knoechel, Gerald N. Evenson, William Watt, 1 and Bruce A. Pearlman (1997). "Production Scale Synthesis of the Non-Nucleoside Reverse Transcriptase Inhibitor Atevirdine Mesylate." *Org. Proc. Res. Dev* 1: 106-116.

Wright, L., X. Barril, et al. (2004). "Structure-activity relationships in purine-based inhibitor binding to HSP90 isoforms." *Chem Biol* 11(6): 775-85.

Yablonski, D., Kane, L. P., Qian, D. and Weiss, A. (1998). "An Nck-Pak1 signaling module is required for T cell receptor-mediated activation of NFAT, but not of JNK." *EMBO J.* 17: 5647-5657.

Yablonski, D., M. R. Kuhne, et al. (1998). "Uncoupling of nonreceptor tyrosine kinases from PLC-gammal in an SLP-76-deficient T cell." *Science* 281(5375): 413-6.

The invention claimed is:

1. A compound of the general formula II:

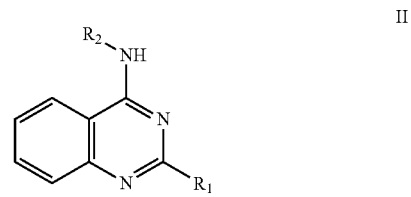

or a compound which is a pharmaceutically acceptable salt or solvate thereof, wherein $R_1$ is trimethoxyphenyl or trihydroxyphenyl; and $R_2$ is phenyl, 4-methylphenyl, 2,4-dimethylphenyl, 4-hydroxyphenyl, 4-methoxyphenyl, 4-octyloxyphenyl, 4-trifluoromethoxyphenyl, 4-chlorophenyl, benzyl, 4-aminobenzyl, 3,4-difluorobenzyl, 3,4-dichlorobenzyl, 4-methoxybenzyl, or 2-hydroxymethylphenyl.

2. The compound of claim 1, wherein $R_1$ is 3,4,5-trimethoxyphenyl or 3,4,5-trihydroxyphenyl.

3. The compound of claim 2, wherein $R_1$ is 3,4,5-trimethoxyphenyl and $R_2$ is 4-methylphenyl.

4. A pharmaceutical composition comprising a compound according to claim 1, and a pharmaceutically acceptable carrier.

5. A method for treatment of a disease, condition or disorder selected from the group consisting of psoriasis, Host-Versus-Graft-Disease (HVGD) and Graft-Versus-Host-Disease (GVHD), in an individual in need thereof, comprising administering to said individual a therapeutically effective amount of a compound of the general formula II:

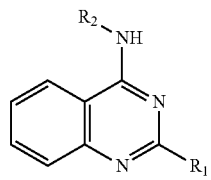

or a compound which is a pharmaceutically acceptable salt or solvate thereof,
wherein
$R_1$ is trimethoxyphenyl or trihydroxyphenyl; and
$R_2$ is phenyl, 4-methylphenyl, 2,4-dimethylphenyl, 4-hydroxyphenyl, 4-methoxyphenyl, 4-octyloxyphenyl, 4-trifluoromethoxyphenyl, 4-chlorophenyl, benzyl, 4-aminobenzyl, 3,4-difluorobenzyl, 3,4-dichlorobenzyl, 4-methoxybenzyl, or 2-hydroxymethylphenyl.

6. The method of claim 5, wherein $R_1$ is 3,4,5-trimethoxyphenyl or 3,4,5-trihydroxyphenyl.

7. The method of claim 5, wherein $R_1$ is 3,4,5-trimethoxyphenyl and $R_2$ is 4-methylphenyl.

8. A topical composition comprising a compound of claim 1, and a topically pharmaceutically acceptable carrier.

9. A method for treatment of a disease, condition or disorder selected from the group consisting of psoriasis, Host-Versus-Graft-Disease (HVGD) and Graft-Versus-Host-Disease (GVHD), in an individual in need thereof, comprising administering to said individual a therapeutically effective amount of the topical composition of claim 8.

10. The topical composition of claim 8, wherein R1 of the compound of claim 1 is 3,4,5-trimethoxyphenyl and R2 is 4-methylphenyl.

11. The method of claim 5 wherein the disease, condition or disorder is psoriasis.

12. The method of claim 5 wherein the disease, condition or disorder is Host-Versus-Graft-Disease (HVGD).

13. The method of claim 5 wherein the disease, condition or disorder is Graft-Versus-Host-Disease (GVHD).

14. The method of claim 9 wherein the disease, condition or disorder is psoriasis.

15. The method of claim 9 wherein the disease, condition or disorder is Host-Versus-Graft-Disease (HVGD).

16. The method of claim 9 wherein the disease, condition or disorder is Graft-Versus-Host-Disease (GVHD).

17. The topical composition of claim 8, wherein $R_1$ of the compound of claim 1 is 3,4,5-trimethoxyphenyl or 3,4,5-trihydroxyphenyl.

18. The method of claim 9, wherein $R_1$ of the compound of claim 1 is 3,4,5-trimethoxyphenyl or 3,4,5-trihydroxyphenyl.

19. The method of claim 9, wherein $R_1$ of the compound of claim 1 is 3,4,5-trimethoxyphenyl and $R_2$ is 4-methylphenyl.

* * * * *